(12) United States Patent
Chouinard et al.

(10) Patent No.: US 11,291,452 B2
(45) Date of Patent: Apr. 5, 2022

(54) MEDICAL DEVICE DEPLOYMENT SYSTEM

(71) Applicant: W. L. Gore & Associates, Inc., Newark, DE (US)

(72) Inventors: Brian D. Chouinard, Flagstaff, AZ (US); Nathan L. Friedman, Flagstaff, AZ (US); Josue Lopez, Flagstaff, AZ (US); Thomas R. McDaniel, Flagstaff, AZ (US); Stanislaw L. Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 507 days.

(21) Appl. No.: 14/315,157

(22) Filed: Jun. 25, 2014

(65) Prior Publication Data

US 2015/0005808 A1     Jan. 1, 2015

Related U.S. Application Data

(60) Provisional application No. 61/839,799, filed on Jun. 26, 2013.

(51) Int. Cl.
| | |
|---|---|
| *A61B 17/00* | (2006.01) |
| *A61F 2/95* | (2013.01) |
| *A61B 17/12* | (2006.01) |
| *A61F 2/24* | (2006.01) |
| *A61F 2/01* | (2006.01) |

(52) U.S. Cl.
CPC .. *A61B 17/12022* (2013.01); *A61B 17/12145* (2013.01); *A61B 17/12168* (2013.01); *A61B 2017/00575* (2013.01); *A61B 2017/1205* (2013.01); *A61B 2017/12054* (2013.01); *A61F 2/011* (2020.05); *A61F 2/2427* (2013.01); *A61F 2/2439* (2013.01); *A61F 2/95* (2013.01); *A61F 2002/9511* (2013.01)

(58) Field of Classification Search
CPC ........ A61B 17/12022; A61B 17/12145; A61B 2017/12054; A61B 17/12168; A61B 2017/00575; A61F 2002/011; A61F 2/01
See application file for complete search history.

(56) References Cited

U.S. PATENT DOCUMENTS

| | | | |
|---|---|---|---|
| 5,160,341 A | * | 11/1992 | Brenneman ............... A61F 2/88 606/198 |
| 5,261,916 A | | 11/1993 | Engelson |
| 5,372,600 A | | 12/1994 | Beyar et al. |
| | | | (Continued) |

FOREIGN PATENT DOCUMENTS

| | | |
|---|---|---|
| EP | 2387959 | 11/2011 |
| EP | 2777542 | 9/2014 |
| | (Continued) | |

OTHER PUBLICATIONS

International Search Report for PCT/US2014/044288 dated Feb. 5, 2015, corresponding to U.S. Appl. No. 14/315,157, 6 pages.

*Primary Examiner* — Jing Rui Ou

(57) ABSTRACT

Deployment systems and methods are provided herein for percutaneous transcatheter deployment of medical devices. A medical device deployment system includes a body member and a body locking member that is configured to cooperatively engage along a portion of the body member such that the body member is releasably coupleable to a medical device.

7 Claims, 12 Drawing Sheets

(56) References Cited

U.S. PATENT DOCUMENTS

| | | | | |
|---|---|---|---|---|
| 5,693,083 A * | 12/1997 | Baker | ............ | A61B 17/11 606/195 |
| 5,925,059 A * | 7/1999 | Palermo | ............ | A61B 17/12022 606/191 |
| 6,039,744 A | 3/2000 | Calsa | | |
| 6,102,942 A | 8/2000 | Ahari | | |
| 6,183,481 B1 * | 2/2001 | Lee | ............ | A61F 2/954 606/108 |
| RE37,117 E * | 3/2001 | Palermo | ............ | A61B 17/12022 128/898 |
| 6,989,024 B2 * | 1/2006 | Hebert | ............ | A61F 2/95 604/264 |
| 7,226,466 B2 | 6/2007 | Opolski | | |
| 7,871,419 B2 | 1/2011 | Devellian et al. | | |
| 8,257,389 B2 | 9/2012 | Chanduszko et al. | | |
| 10,076,336 B2 * | 9/2018 | Kleshinski | ............ | A61B 17/12031 |
| 2002/0133191 A1 * | 9/2002 | Khosravi | ............ | A61F 2/01 606/200 |
| 2002/0151955 A1 * | 10/2002 | Tran | ............ | A61F 2/95 623/1.12 |
| 2003/0225446 A1 * | 12/2003 | Hartley | ............ | A61F 2/95 623/1.11 |
| 2004/0106977 A1 * | 6/2004 | Sullivan | ............ | A61F 2/95 623/1.12 |
| 2004/0138734 A1 * | 7/2004 | Chobotov | ............ | A61F 2/954 623/1.11 |
| 2006/0004433 A1 * | 1/2006 | Greenberg | ............ | A61F 2/07 623/1.11 |
| 2006/0122647 A1 | 6/2006 | Callaghan et al. | | |
| 2007/0049970 A1 | 3/2007 | Belef | | |
| 2008/0300616 A1 * | 12/2008 | Que | ............ | A61B 17/12022 606/191 |
| 2009/0105801 A1 * | 4/2009 | Ivancev | ............ | A61F 2/954 623/1.11 |
| 2010/0121350 A1 | 5/2010 | Mirigian | | |
| 2011/0202085 A1 * | 8/2011 | Loganathan | ............ | A61B 17/12022 606/200 |
| 2012/0296409 A1 * | 11/2012 | Kawakita | ............ | A61F 2/915 623/1.12 |
| 2014/0067037 A1 * | 3/2014 | Fargahi | ............ | A61F 2/966 623/1.12 |
| 2014/0180385 A1 * | 6/2014 | Majercak | ............ | A61F 2/954 623/1.12 |

FOREIGN PATENT DOCUMENTS

| | | |
|---|---|---|
| WO | 2007/106495 | 9/2007 |
| WO | WO-2007106495 A2 | 9/2007 |
| WO | WO-2007121405 A2 | 10/2007 |
| WO | WO-2008127525 A1 | 10/2008 |
| WO | WO-2009132045 A2 | 10/2009 |

* cited by examiner

Section A-A

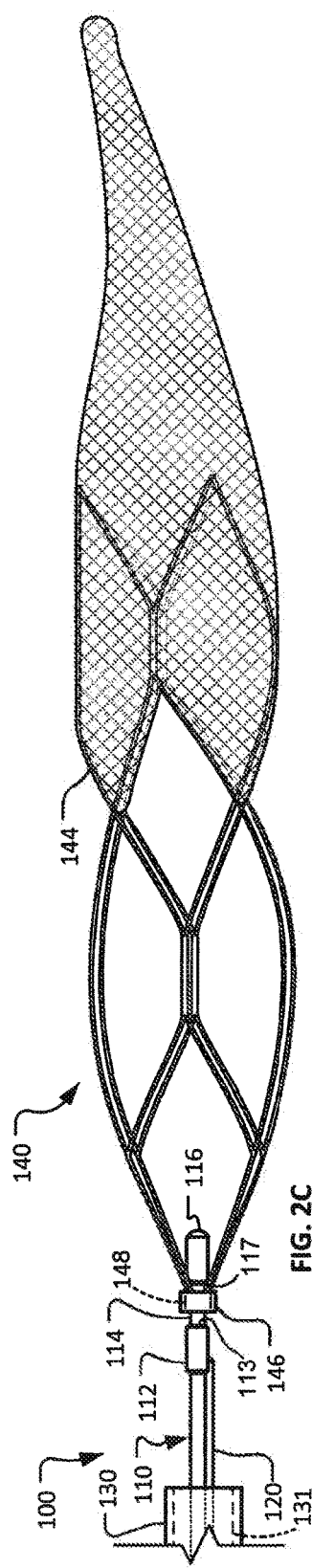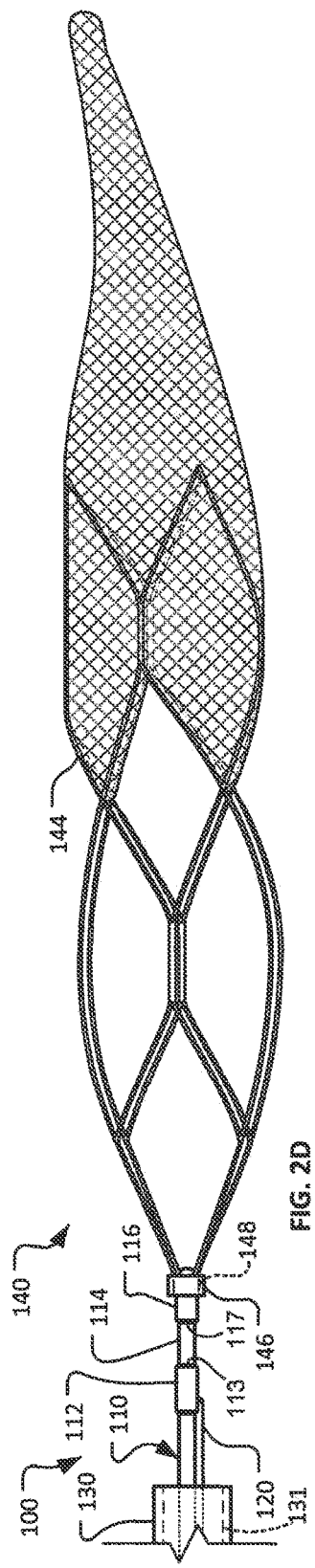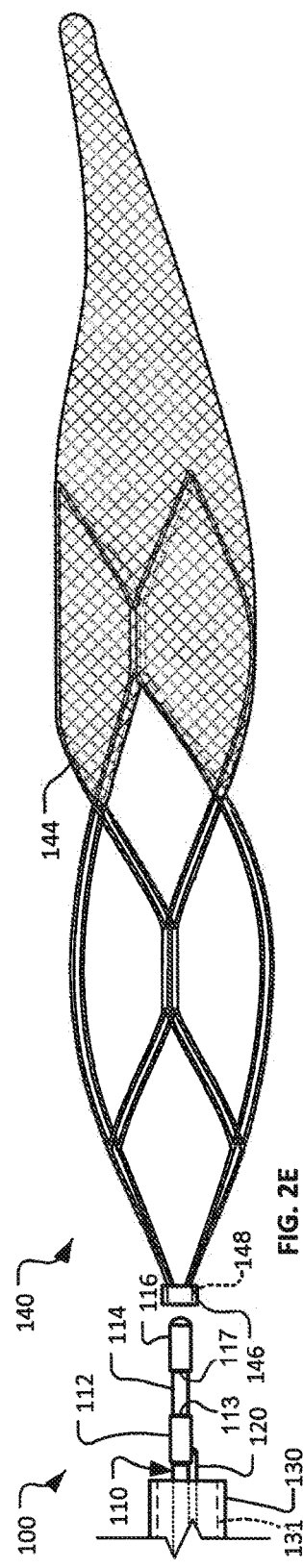

Section C-C

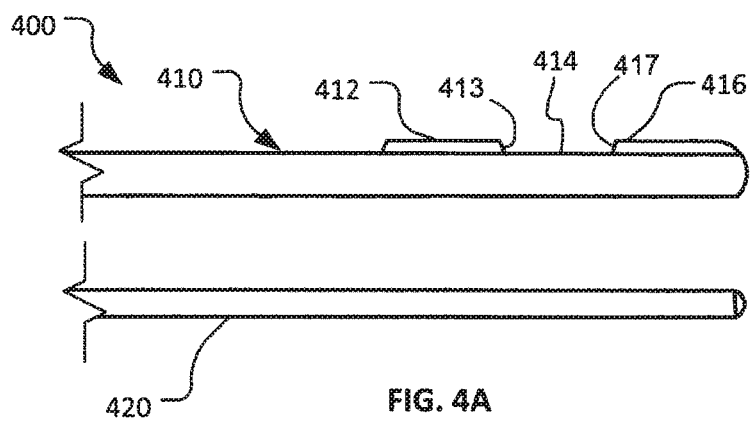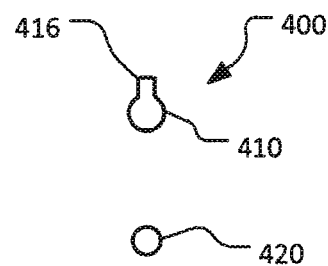
FIG. 4A
FIG. 4B
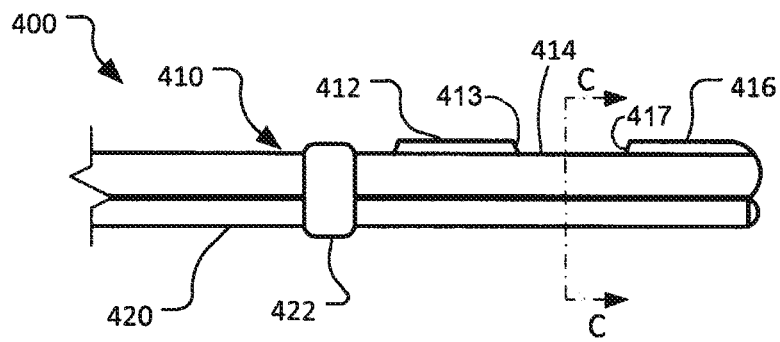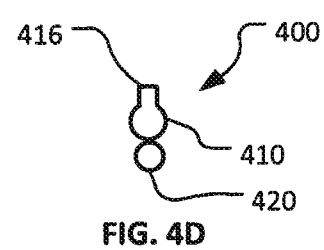
FIG. 4C
FIG. 4D
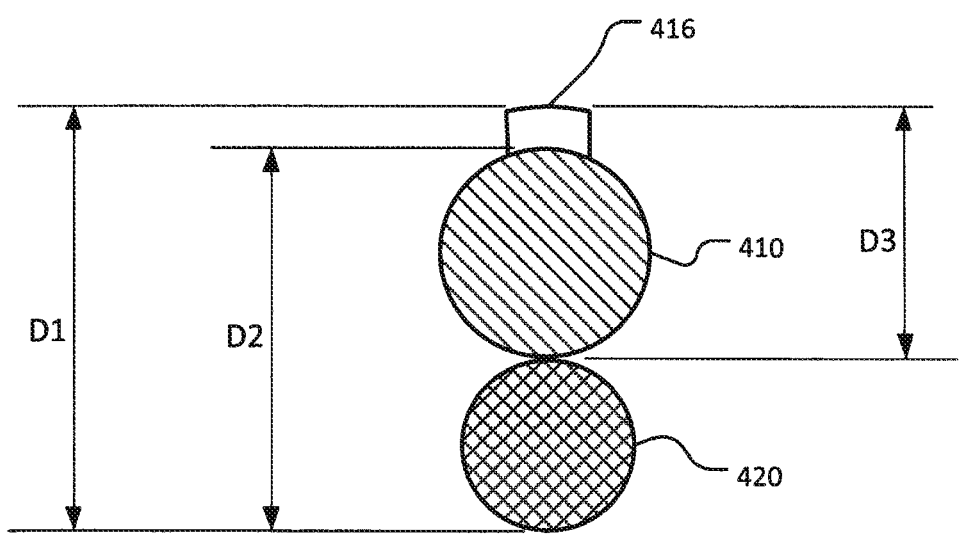
Section C-C
FIG. 4E

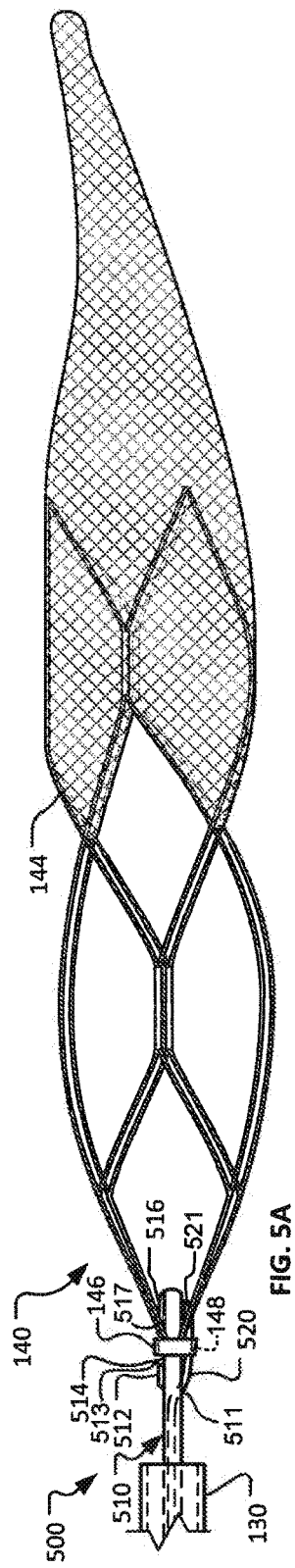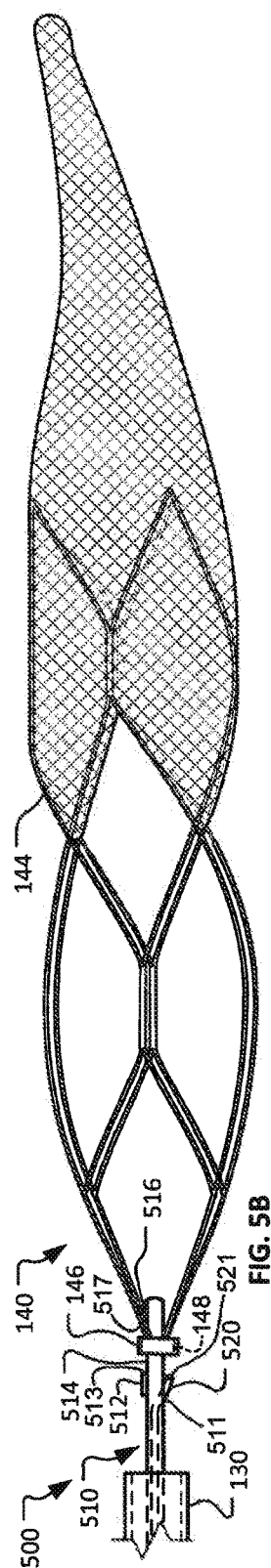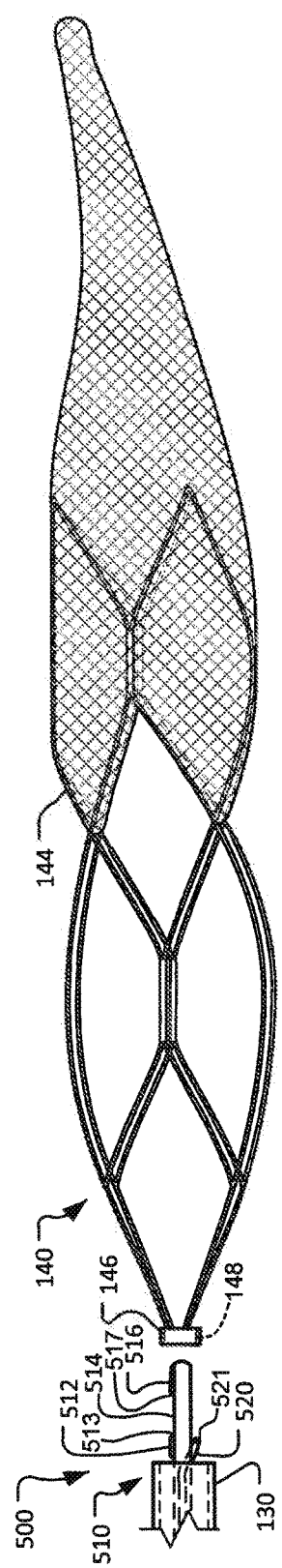

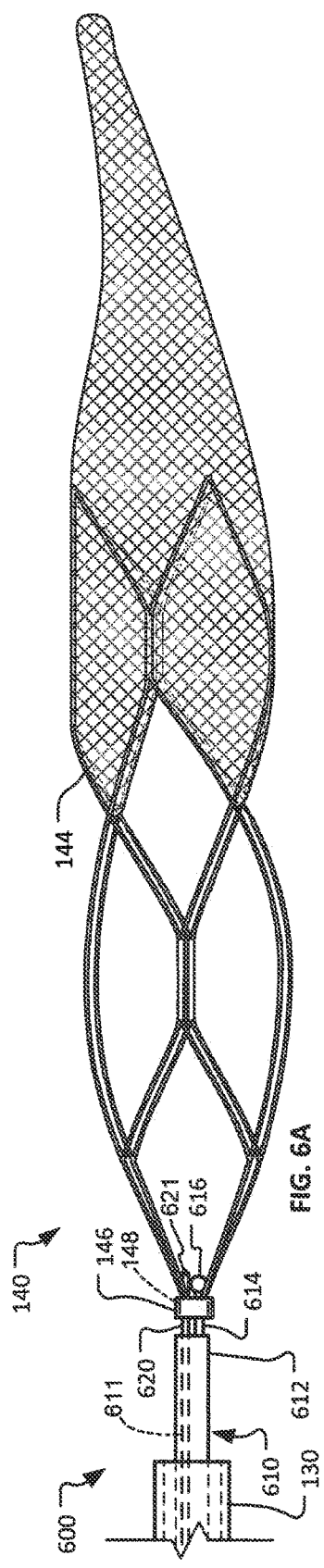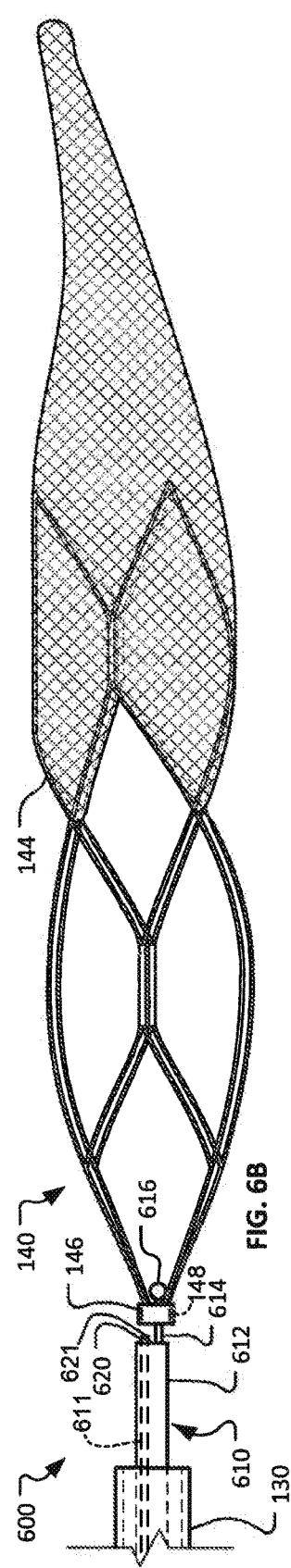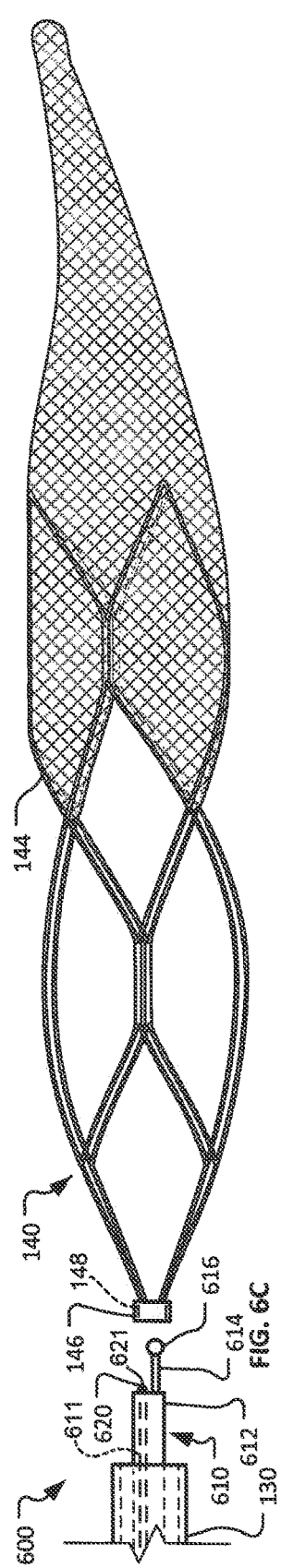

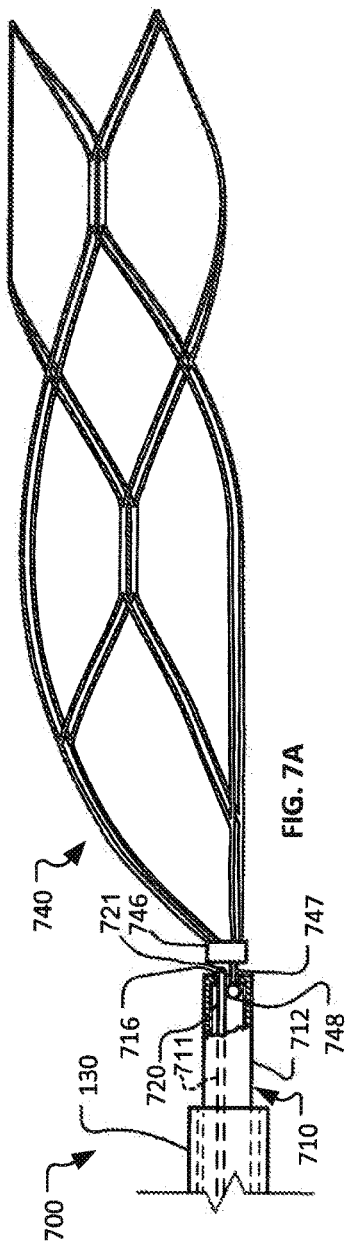
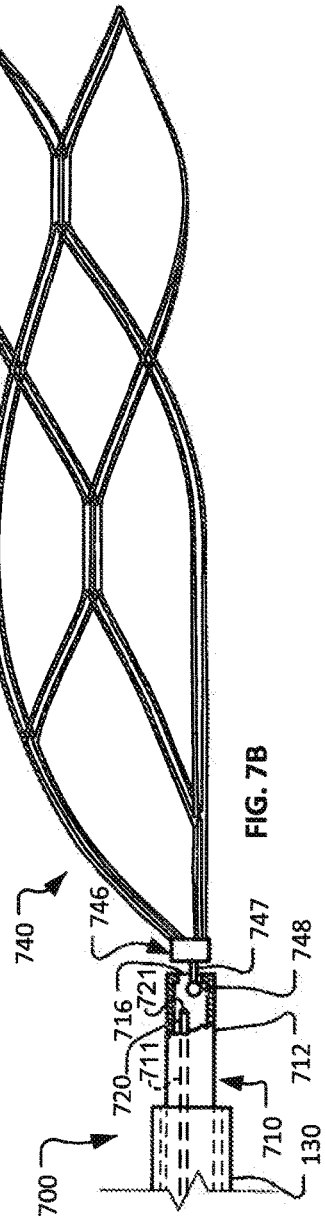
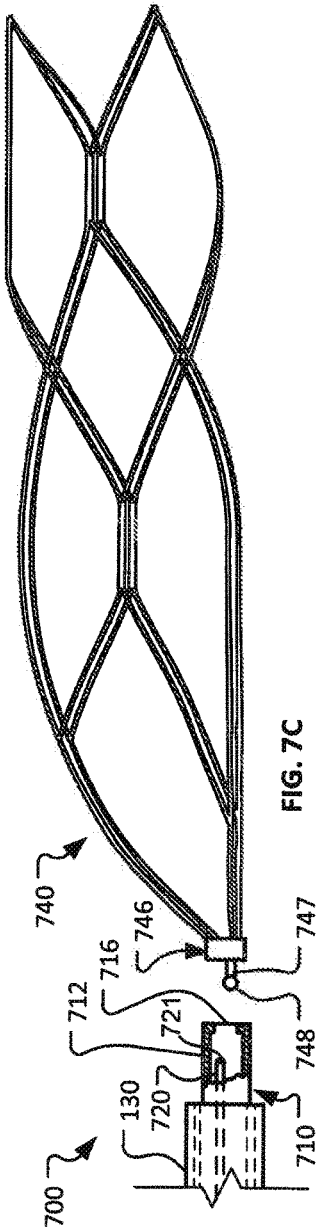

MEDICAL DEVICE DEPLOYMENT SYSTEM

TECHNICAL FIELD

This document relates to deployment systems and methods for percutaneous transcatheter deployment of medical devices. For example, a medical device deployment system includes a body member and a body locking member that is configured to cooperatively engage along a portion of the body member such that the body member is releasably coupleable to a medical device.

BACKGROUND

A wide variety of known medical devices can be implanted within a patient's body to provide interventional or remedial treatments. Occlusion devices, for example, can be implanted to close holes in septa. An atrial septal defect (ASD) in the heart is an abnormal opening in the septum between the left and right atria of the heart, and is one such condition that can be treated by implanting an occlusion device. A ventricular septal defect (VSD) in the heart is an abnormal opening in the septum between the left and right ventricles of the heart, and is another condition that can be treated by implanting an occlusion device.

Occlusion devices can also be implanted to block or occlude undesired conduits, fistulae, or ostia, such as saphenous veins. For example, the left atrial appendage (LAA) is a closed cavity that looks like a small thumb or windsock, and is connected to the anterolateral wall of the left atrium between the mitral valve and the root of the left pulmonary vein. The LAA contracts with the left atrium during a normal heart cycle and keeps blood therein from becoming stagnant. However, with atrial fibrillation, the LAA often fails to contract with any vigor due to disorganized electrical signals. As a result, thrombi can be predisposed to form in the stagnant blood within the LAA. An implantable medical device can be used to block off the LAA to prevent an escape of thrombi from the LAA, preventing introduction of the thrombi to an individual's vasculature. Other types of known medical devices, such as filters and stents, can be also implanted in patients to treat a wide variety of disorders.

Many medical devices are delivered to a deployment site using minimally invasive transcatheter techniques. In such cases, the medical device is typically configured in a collapsed or low-profile arrangement and delivered to the internal deployment site via a delivery sheath. At the deployment site, the medical device is ejected from the delivery sheath and expands to a larger size to provide effective treatment of the particular medical condition, such as occluding an ASD, VSD, or LAA, or stenting a vein or artery. In some cases, a delivery device (e.g., an elongate member such as a guidewire, tubular polymer catheter, solid polymer catheter, and the like) is attached to the implantable medical device and is used to advance the collapsed implantable medical device within the delivery sheath through to the desired deployment site in the patient's body.

One example delivery system attaches the delivery device to the implantable medical device via a threaded screw-type attachment. For example, the implantable medical device may include a female threaded receptacle that is configured to receive a male threaded portion of the delivery device, and the delivery device is attached to the medical device in this manner. After the implantable device is deployed from the delivery sheath at the deployment site, a clinician operator provides a rotational force at a proximal end of the delivery device to cause the delivery device to unscrew, and detach, from the implantable device.

SUMMARY

Deployment systems and methods are described herein that are useful, for example, for controllably deploying medical devices in desired positions within body cavities, conduits, organs, tissues, and vessels. The systems and methods provided herein can be used for the percutaneous transcatheter deployment of medical devices. Alternatively, the systems and methods provided herein can be used to deliver medical devices via a natural body orifice or passage. In some embodiments, the systems and methods provided herein can be used for laproscopic procedures, or with other devices in the GI tract that benefit from the ability of the deployment system to push and pull the medical device during the deployment process. In an example embodiment, a deployment system and method for deploying a medical device comprising a self-expanding frame with a covering is provided.

Particular embodiments of the subject matter described in this specification can be implemented so as to realize one or more of the following advantages. The deployment devices provided herein are low-profile, thereby enabling the use of minimally-sized deployment sheaths that are used to contain and transport the deployment devices to a target site within a patient's body. As such, the deployment systems are well-suited for use in clinically challenging scenarios such as tortuous path anatomies, small vessels, and the like. The deployment systems also have a positive release mechanism, which is also advantageous for use in tortuous path anatomies. The low-profile nature of the deployment systems also makes them suitable for deploying very small medical devices. In some embodiments, the deployment systems are capable of exerting both pushing and pulling forces on the medical device being deployed. The deployment systems can thereby be used to deploy medical devices in a controlled manner, such that the medical devices can be accurately positioned and released as desired by a clinician operator. Further, the deployment systems and techniques provided herein can be used to accurately control the positioning of a medical device without being overly complex for a clinician to operate.

In one general aspect, a delivery system for delivering a medical device in a body is provided. The delivery system comprises a body member having a nominal diameter, a distal end, and a proximal end. A distal end portion of the body member has at least one portion having an increased diameter from the nominal diameter of the body member. The delivery system also comprises a body locking member having a nominal diameter, a distal end and a proximal end. The body locking member is configured to cooperatively engage along at least the distal end portion of the body member such that the body member is releasably coupleable to a medical device.

In various implementations, the medical device may comprise an attachment feature that defines an aperture with an inner diameter. The inner diameter of the attachment feature may be less than the combined diameter of the body locking member and the portion of the body member having an increased diameter from the nominal diameter. The inner diameter may be greater than the combined diameter of the body locking member and the nominal diameter of the body member. The inner diameter of the attachment feature may be greater than a diameter of the portion of the body member having an increased diameter from the nominal diameter.

The body member may have two portions that each have an increased diameter from the nominal diameter. The two portions may be spaced apart from each other by a distance to thereby define a coupling portion of the body member that may be configured to releasably couple with the attachment feature. The coupling portion of the body member may have the nominal diameter. One or both of the body member and the body locking member may be comprised of a super-elastic metallic material. One or both of the body member and the body locking member may be comprised of nitinol. The delivery system may further comprise a sheath that is arranged to allow the medical device to pass through a lumen of the sheath when the medical device is coupled to the body member and the body locking member. The delivery system may further comprise a deployment actuator coupled to each of the body member, the body locking member, and the sheath, wherein the deployment actuator is arranged to control positioning of the medical device. The body locking member may cooperatively engage in a groove in an outer surface of the body member. The enlarged portion may comprise a cylindrical segment. The enlarged portion may comprise a radial protrusion.

In another general aspect, a system is provided that comprises a medical device having an interface region; a body member having at least three regions, a first region with a first cross-sectional area, a second region with a second cross-sectional area, and a third region with a third cross-sectional area, wherein the interface region of the medical device is cooperatively engageable with the second region; and a locking member that is adapted to move relative to the body member between at least a first position and a second position, wherein, when the interface region of the medical device is cooperatively engaged with the second region and the locking member is in the first position, the interface region of the medical device is retained between the first and third regions of the body member, and when the locking member is in the second position the interface region of the medical device is releasable from the body member.

In various implementations, the second region may be between the first region and the third region. The locking member may be in contact with the second region when the locking member is in the first position, and the locking member may be out of contact with the second region when the locking member is in the second position. The second cross-sectional area may be less than the first cross-sectional area, and the second cross-sectional area may be less than the third cross-sectional area. The interface region may define an aperture that is cooperatively engageable with the second region. One or both of the body member and the locking member may be comprised of a super-elastic metallic material. One or both of the body member and the locking member may be comprised of nitinol. The system may further comprise a sheath that is arranged to allow the medical device to pass through a lumen of the sheath when the medical device is coupled to the body member. The system may further comprise a deployment actuator coupled to each of the body member, the locking member, and the sheath, and wherein the deployment actuator may be arranged to control positioning of the medical device. The first and third regions may be cylindrical segments. The first and third regions may include radial protrusions. The body member may include a groove in at least a portion of the outer surface of the body member, and at least a portion of the locking member may be engaged in the groove.

In another general aspect, a method of deploying a medical device within a body is provided. The method comprises: providing a delivery system, configuring a medical device in a delivery configuration within the deployment sheath, advancing a distal end of the deployment sheath to a target deployment site within the body; and deploying the medical device. The delivery system comprises: a body member having a nominal diameter, a distal end and a proximal end, wherein a distal end portion of the body member has at least one portion having an increased diameter from the nominal diameter of the body member; a body locking member having a nominal diameter, a distal end and a proximal end, wherein the body locking member is configured to cooperatively engage along at least the distal end portion of the body member such that the body member is releasably coupleable to an attachment feature of the medical device; and a deployment sheath. In various implementations, the delivery configuration may comprise coupling the attachment feature with the body member and the body locking member; and arranging the medical device in a low-profile configuration. Deploying the medical device may comprises moving the deployment sheath in relation to the body member and the body locking member to cause the medical device to emerge out of the deployment sheath; retracting the body locking member proximally in relation to the body member such that the distal tip of the body locking member is positioned proximally of the attachment feature; and retracting the body member to disengage the body member from the attachment feature. The medical device may be an occluder or a filtration device.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 2C-2E are a series of illustrations depicting the example deployment system of FIGS. 1A-1E deploying the medical device.

FIG. 4A depicts the distal end portions of another example deployment system, in accordance with some embodiments.

FIG. 4B illustrates an end view of the distal end portions of the deployment system of FIG. 4A.

FIG. 4C illustrates the distal end portions of the deployment system of FIG. 4A in an engaged configuration.

FIG. 4D illustrates an end view of the engaged distal end portions of the deployment system in correspondence with FIG. 4C.

FIG. 4E is a cross-sectional view of the engaged distal end portions of the deployment system of FIG. 4C.

FIGS. 5A-5C are a series of illustrations depicting the deployment of a medical device using another example deployment system.

FIGS. 6A-6C are a series of illustrations depicting the deployment of a medical device using another example deployment system.

FIGS. 7A-7C are a series of illustrations depicting the deployment of a medical device using another example deployment system.

Like reference numbers and designations in the various drawings indicate like elements.

DETAILED DESCRIPTION

Figure 1A:
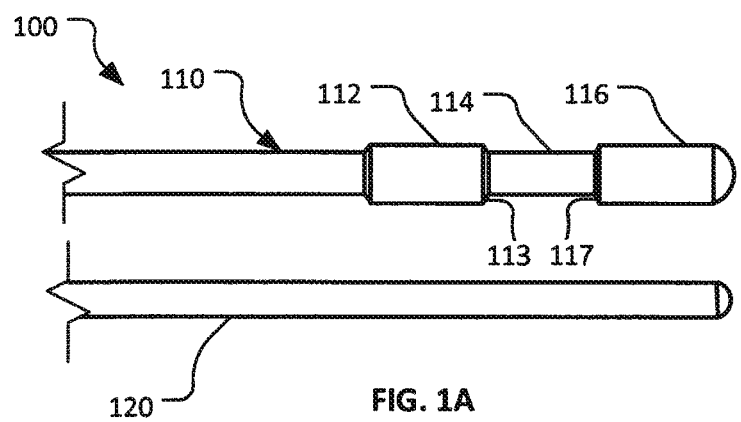
FIG. 1A depicts the distal end portions of an example deployment system, in accordance with some embodiments.
Figure 1B:
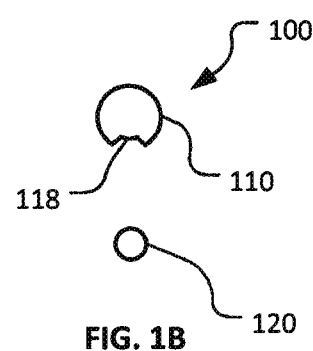
FIG. 1B illustrates an end view of the distal end portions of the deployment system of FIG. 1A.
Figure 1C:
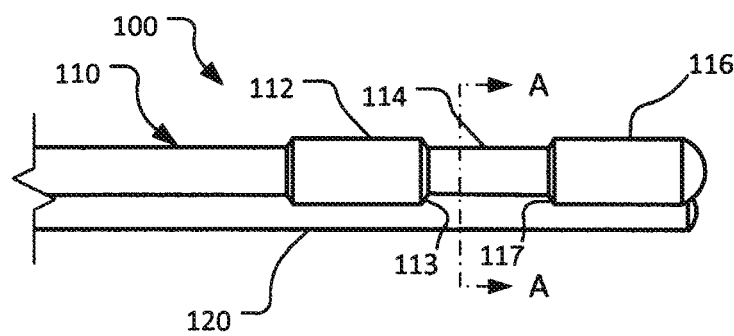
FIG. 1C illustrates the distal end portions of the deployment system of FIG. 1A in an engaged configuration.
Figure 1D:
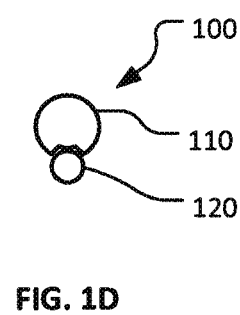
FIG. 1D illustrates an end view of the engaged distal end portions of the deployment system in correspondence with FIG. 1C.

This document provides deployment systems and methods that are useful, for example, for controllably deploying medical devices at desired locations, such as within body cavities, conduits, organs, tissues, and vessels. For example, the systems and methods provided herein can be used for percutaneous transcatheter deployment of medical devices. Embodiments can be utilized to deliver a variety of medical devices including occluders (e.g., LAA occluders), filters (e.g., inferior vena cava filters or embolic filters), and stents.

Medical devices can be deployed at a target site within the patient using the systems and methods provided herein. To deploy a medical device at a target site in a patient, in some embodiments a deployment sheath is inserted into the patient and the distal tip of the deployment sheath is directed to the target site. In some cases, the deployment sheath is installed over a guidewire or a guide catheter that has been previously placed in the patient. In some embodiments, the medical devices are removably coupled to one or more elongate delivery control devices, and the medical device is collapsed to a low-profile configuration. In the low-profile configuration, the medical device can be inserted into the deployment sheath and transmitted through the deployment sheath to the distal tip of the deployment sheath. A clinician can manipulate the elongate delivery control devices to move the collapsed medical device within the deployment sheath and to cause the medical device to emerge from the deployment sheath at the target delivery site. For some embodiments of medical devices, the medical device then reconfigures to an expanded configuration at or near the target site upon deployment from the sheath. The clinician then manipulates the elongate delivery control device to decouple the elongate delivery control device from the medical device, and the deployment sheath and elongate delivery control device are removed from the patient. The systems and methods provided herein enable a controllable deployment process, whereby a clinician operator can control the positioning of the medical device in a desired position prior to releasing the device.

FIGS. 1A-1E depict the distal portions of two elongate delivery control devices that comprise an example deployment system 100. The deployment system 100 includes a body member 110, a body locking member 120, a deployment sheath (not shown), and, optionally, a deployment actuator (not shown). The deployment system 100 is configured for the transcatheter deployment of a medical device (not shown) at a desired location in the body of a patient. These distal portions of the body member 110 and the body locking member 120 have features that are configured such that the body member 110 can be releasably coupled with the medical device as explained further herein. The proximal end portions (not shown) of the body member 110 and the body locking member 120 can be handled and manipulated by a clinician to controllably perform the deployment process as explained further herein. In some cases, the proximal portions of the body member 110 and the body locking member 120 are coupled to a deployment actuator mechanism (not shown) to provide convenient control to the clinician. In some cases, the proximal portions (or any portion of the body member 110 that is proximal of the distal portions) of the body member 110 and the body locking member 120 are handled directly by the clinician without the use of a deployment actuator. While the example deployment system 100 and other embodiments provided herein generally use the distal portions of the body member 110 and body locking member 120 to couple with a medical device to be deployed, in some embodiments portions of the body member 110 and body locking member 120 that are proximal of the distal portions (e.g., portions anywhere between the proximal and distal ends) can be used to releasably couple with the medical device to be deployed.

In some embodiments, the body member 110 and the body locking member 120 are elongate members such as wires, shafts, tubes, or rods, and the like. A variety of lengths and nominal diameters of the body member 110 and the body locking member 120 can be used. As used herein, "nominal diameter" refers to the outer diameter of circular cross-sectional shapes (or the maximum outer profile dimension for non-circular cross-sectional shapes) of the majority of the body member 110 or the body locking member 120. In general, suitable lengths and nominal diameters of the body member 110 and the body locking member 120 can be selected to accommodate one or more of the particular medical device to be deployed, the patient, the delivery sheath, and the implantation procedure to be used, for example. In some embodiments, the nominal diameters of the body member 110 and the body locking member 120 are about 0.1 to 5.0 millimeters, or about 0.2 to 3.0 millimeters, or about 0.3 to 1.5 millimeters. In some embodiments, the lengths of the body member 110 and the body locking member 120 are about 20 to 200 cm, or about 40 to 150 cm, or about 60 to 100 cm. In general, any practical nominal diameter and length of the body member 110 and the body locking member 120 are envisioned as within the scope of this disclosure. In some embodiments, the body member 110 and the body locking member 120 are the same diameter. In some embodiments, one of either the body member 110 or the body locking member 120 is larger than the other of the body member 110 or the body locking member 120. That is, in some embodiments the body member 110 is larger than the body locking member 120, and in some embodiments the body locking member 120 is larger than the body member 110.

The body member 110 and the body locking member 120 can be made from various types of materials. The body member 110 and the body locking member 120 can be made from the same material or from different materials. In some embodiments, the body member 110 and the body locking member 120 are both made from metals. For example, nitinol (NiTi), other super-elastic alloys, titanium, titanium alloys, stainless steels, and other types of metal materials can be used to construct the body member 110 and the body locking member 120. In some embodiments, the body member 110 and the body locking member 120 are both made from polymers. For example, nylon, Pebax, polytetrafluoroethylene (PTFE), polymide, polyetheretherketone (PEEK), and other types of polymers can be used to construct the body member 110 and the body locking member 120. In some embodiments, a combination of two or more materials are used to construct the body member 110 and/or the body locking member 120. In some embodiments, the material or materials of construction is/are braided, twisted, coiled, or the like. In some embodiments, polymeric materials are used to construct the body member 110 and/or the body locking member 120. In some embodiments, a combination of metallic and polymeric materials are used to construct the body member 110 and/or the body locking member 120. For example, in some embodiments the majority of the body member 110 is metal and the raised or enlarged portions at the distal end of the body member 110 are made of polymers. In another example, a polymer body member 110 or polymer body locking member 120 can be reinforced with a metal such as stainless steel or nitinol.

In some embodiments, radiopaque materials are included on or in the body member 110 and/or the body locking member 120. For example, in some embodiments radiopaque marker bands are included on portions of the body member 110 and/or the body locking member 120. In some embodiments, the core of the body member 110 and/or the body locking member 120, or portions thereof, includes a radiopaque material such as platinum. For example, the body member 110 and/or the body locking member 120 can be comprised of a nitinol drawn tube with a platinum core. In some embodiments, a radiopaque coating is applied to the body member 110 and/or the body locking member 120. Such radiopaque markers can enable assessment of the medical device's position and orientation at the deployment site by enabling the clinician operator to visualize the device's positioning in relation to surrounding tissue using MRI, x-ray, or other visualization techniques. In some embodiments, a lubricious coating, such as a hydrophilic coating or PTFE coating, is applied to one or more of the body member 110, the body locking member 120, and the delivery sheath to make the body member 110 and the body locking member 120 easier to move relative to each other by the clinician. In some embodiments, portions of the body member 110 or body locking member 120 that are proximal of the distal portions can be made with a smaller diameter than the distal portions to make the body member 110 and the body locking member 120 easier to move relative to each other by the clinician.

In some embodiments, the elongate delivery control devices of a deployment system can be configured to cooperatively engage with each other. In the deployment system 100, for example, the body locking member 120 is configured to cooperatively engage with the body member 110. The engagement can be facilitated by a groove 118 that is defined on the outer surface of the body member 110. In some embodiments, a groove can be defined on the outer surface of the body locking member 120. The groove 118 is sized and configured to receive at least a portion of the body locking member 120. In some embodiments the groove 118 does not substantially inhibit axial translational movements of the body member 110 and the body locking member 120 in relation to each other. In some embodiments, the groove 118 is configured to provide a selected amount of resistance to axial translation movement between the body member 110 and the body locking member 120. The cooperative engagement between the body member 110 and the body locking member 120 enables alignment therebetween, and can mitigate the potential for undesirable twisting of the body member 110 with the body locking member 120. Such twisting could inhibit the axial movements of the body member 110 and the body locking member 120 relative to each other. In some embodiments, the body member 110 and the body locking member 120 are configured to cooperatively engage with each other along substantially their entire lengths. In some embodiments, the body locking member 120 is configured to cooperatively engage along at least the distal portion of the body member 110. In some embodiments, the body locking member 120 is configured to cooperatively engage along a portion or portions of the body member 110 that are not at the distal portion of the body member 110.

In some embodiments, one or both of the body member 110 and the body locking member 120 can include one or more collars or sleeves through which the other of the body member 110 or the body locking member 120 passes. The use of such collars or sleeves can provide additional resistance against twisting (e.g., refer to FIG. 4C).

In some embodiments, the body member 110 includes a first enlarged portion 112, a coupling portion 114, and a second enlarged portion 116. In some embodiments, the first enlarged portion 112 and second enlarged portion 116 are regions of the body member 110 that have a different axial or cross-sectional profile than the majority of the body member 110. In various embodiments, the first enlarged portion 112 can extend in the proximal direction a substantial length or the entire length of the body member 110. As used herein, the term "enlarged," when used in the context of the enlarged portions of the body member 110, refers to a change in axial or cross-sectional profile including, but not limited to, an increased diameter, a greater cross-sectional area, a protrusion, and a reconfiguration of the axial profile such as from a bend or a crimp that does not necessarily increase the cross-sectional area. In some embodiments, the enlarged portions 112 and 116 may also be formed by the inflation of one or more inflatable balloon devices on the body member 110.

In some embodiments, the first enlarged portion 112 and the second enlarged portion 116 are cylindrical segments. In some embodiments, various other shapes and reconfigurations of the body member 110 profiles can be used to provide enlarged portions. In some embodiments, the first enlarged portion 112 is at least as large and may be larger than the second enlarged portion 116. While in some embodiments the first portion and the second portion have similar profiles (e.g. shape, size), in some embodiments the first portion and second portion have different profiles.

The first enlarged portion 112 and second enlarged portion 116 can be constructed in a variety of ways. In some embodiments, the body member 110 is manufactured using a rotary grinding process and the nominal portions of the body member 110 are ground to a smaller diameter than the first enlarged portion 112 and second enlarged portion 116. In some embodiments, the first enlarged portion 112 and second enlarged portion 116 are sleeves that are fastened to the body member 110 using an interference fit, gluing, crimping, welding, pinning, and the like. In some embodiments, the first enlarged portion 112 and second enlarged portion 116 are over-molded, cast, or extruded onto the body member 110. In some embodiments, a secondary machining process can be performed to create the groove 118. In some embodiments, groove side walls are built-up on one surface of the body member 110 or the body locking member 120 to form a groove.

The first enlarged portion 112 and second enlarged portion 116 are positioned relative to each other to define the coupling portion 114 in the region between the first enlarged portion 112 and second enlarged portion 116. The coupling portion 114 is a region of the body member 110 that has a different profile (e.g., a smaller diameter or cross-sectional area) than the first enlarged portion 112 and second enlarged portion 116. In some embodiments, the coupling portion 114 has the same profile, diameter, or cross-sectional area as the nominal diameter of the body member 110. In some embodiments, the coupling portion 114 has a dissimilar profile, diameter, or cross-sectional area as compared to the nominal diameter of the body member 110. In the illustrated embodiments, the coupling portion 114 has a reduced outer peripheral dimension with respect to the first and second enlarged portions 112, 116. The first and second enlarged portions 112, 116 define respective first and second locking surfaces 113, 117. The coupling portion 114 extends axially between the first and second locking surfaces 113, 117. Thus, the first and second locking surfaces 113, 117 are axially spaced apart and extend outwardly from the coupling portion 114.

Figure 1E:
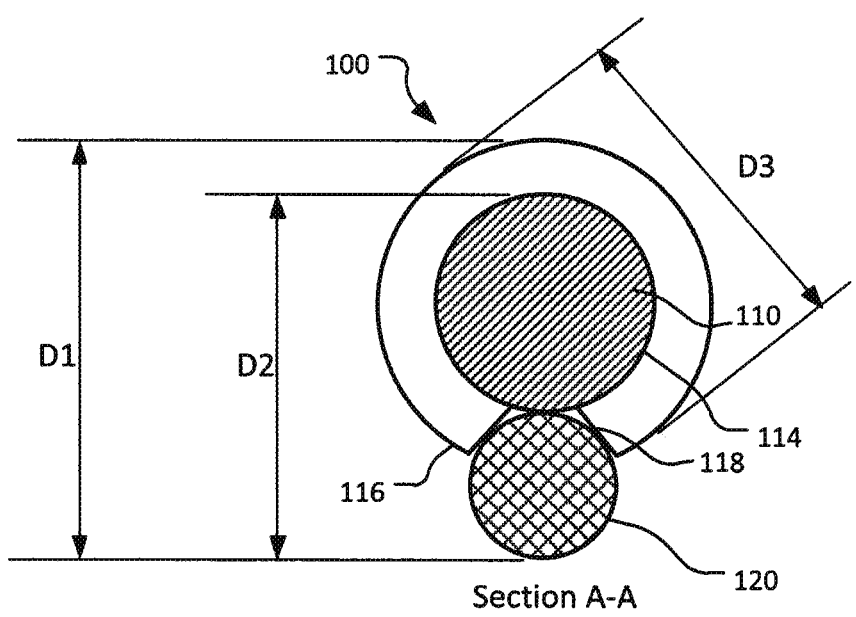
FIG. 1E is a cross-sectional view of the engaged distal end portions of the deployment system of FIG. 1C.

FIG. 1E is a cross-sectional view of the body member 110 and the body locking member 120 taken at the plane indicated at A-A in FIG. 10 illustrating the coupling portion 114, and with the body member 110 and the body locking member 120 in engagement with each other. The combination of the body member 110 and the body locking member 120 creates certain physical dimensional aspects that are used advantageously by the deployment system 100, as will be explained further herein. More specifically, a dimension D1 is defined that spans a maximum distance between the outer surface of the second enlarged portion 116 and the outer surface of the body locking member 120. A dimension D2 is defined that spans a maximum distance between the outer surface of the coupling portion 114 and the outer surface of the body locking member 120. And a dimension D3 is a maximum outer dimension of the second enlarged portion 116.

Figure 2A:
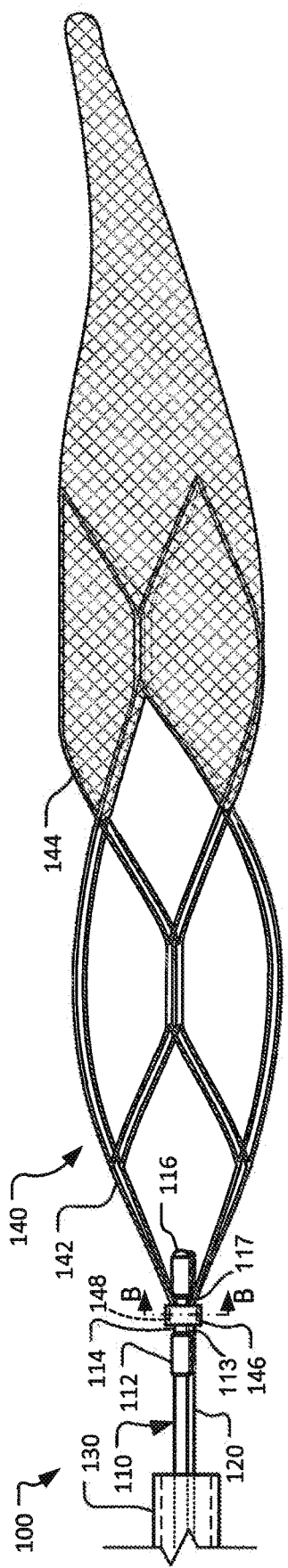
FIG. 2A illustrates the example deployment system of FIGS. 1A-1E coupled to a medical device.

FIG. 2A depicts the example deployment system 100, including a deployment sheath 130, coupled to an example medical device, as generally indicated at 140. The deployment sheath 130 is used to percutaneously deliver the medical device 140 to a target delivery site in the body of a patient. The deployment sheath 130 defines a lumen 131 that can contain the body member 110, the body locking member 120, and the medical device 140 when the medical device 140 is configured in a low-profile or delivery configuration. When the distal end of the deployment sheath 130 is located at or near the desired target delivery site, the clinician can eject the medical device 140 using the body member 110 and the body locking member 120 to make the medical device 140 emerge from the lumen of the deployment sheath 130 as shown in FIG. 2A. The clinician can further manipulate the deployment system 100 to decouple the medical device 140 from the body member 110 as explained further herein.

The deployment sheath 130 can comprise, for example, a polymeric tube that is used to constrain the medical device 140, and to percutaneously deliver the medical device 140 to a target deployment site, such as within a body cavity, tissue, organ, conduit, or vessel. The deployment sheath 130 can have one lumen or multiple (e.g., two or more) lumens. In some embodiments inner and/or outer walls of the deployment sheath 130 are coated with a lubricous material. As shown, the lumen 131 of the deployment sheath 130 can contain the medical device 140, and in this embodiment the medical device 140 is configured in a collapsed or low-profile delivery configuration when the medical device 140 is contained in the lumen 131 of the deployment sheath 130. The tubular deployment sheath 130 can have a circular cross-section or another cross-sectional shape, such as ovular or other suitable shapes. In some embodiments, the proximal portion of the deployment sheath 130 is attached to a deployment actuator (e.g., a handheld deployment actuator or a non-handheld deployment actuator) that can be operated by a clinician operator. In some embodiments, the deployment actuator may provide one or more controls that permit an operator to control one or more aspects of the deployment sheath 130. In some embodiments, the deployment sheath 130 is a steerable deployment sheath. In some embodiments, at least the distal portion of the deployment sheath 130 is steerable. In some embodiments, a guidewire may be installed in the patient first, and the deployment sheath 130 may be installed over or on the guidewire.

The medical device 140 is provided as an example device so as to help illustrate the deployment system 100 and other deployment systems provided herein. But, the deployment systems and methods provided herein can also be used with many other types of medical devices. The example medical device 140 can be used to occlude a structure or a conduit, such as an LAA, vessel, or other structure within the body. Further non-limiting examples of medical devices that are deployable using the systems and methods provided herein include vascular medical devices, patent ductus arteriosus (PDA) medical devices, ASD occluders, cardiac plugs, vascular occluders, IVC filters, coils, grafts, embolic filters, stent graft devices, electrodes, probes, leads, leadless heart surveillance devices, heart valve frames or stents, shunts, biosensors, and others. For further information regarding additional non-limiting examples of medical devices that the deployment systems and methods disclosed herein can be used with, see co-pending U.S. patent application Ser. No. 13/802,428 titled, "Devices and Systems for Thrombus Treatment," filed 14 Aug. 2012, with Edward H. Cully, Nathan L. Friedman, and Eric H. Zacharias as inventors, the entire contents (including the figures) of which are hereby incorporated by reference for all purposes. For further information also regarding additional non-limiting examples of medical devices that the deployment systems and methods disclosed herein can be used with, and for example discussions regarding making the devices, see co-pending U.S. patent application Ser. No. 13/741,665 titled, "Occlusive Devices," filed 13 Sep. 2012, with Coby C. Larsen, Steven J. Masters, and Edward E. Shaw as inventors, the entire contents (including the figures) of which are hereby incorporated by reference for all purposes.

As described above, some medical devices are configured in a collapsed low-profile delivery configuration for containment within a deployment sheath, and then the device reconfigures to an expanded configuration at the delivery site upon deployment from the sheath. To that end, the example medical device 140 is shown in its deployed or expanded configuration. That is, the example medical device 140 is shown in an expanded configuration similar to the configuration that the example medical device 140 would have at a target deployment site within a body. However, prior to its deployment, the example medical device 140 can be contained within the deployment sheath 130, and the medical device 140 can be in a collapsed configuration so as to fit within the deployment sheath 130. The systems and methods provided herein can be used to deploy medical devices, such as example medical device 140, from the deployment sheath 130 to a target deployment site within a body in a controllable fashion. Optionally, a secondary or intermediate sheath or constraining sleeve can be utilized to releasably constrain the medical device at an intermediate state, which is larger than the collapsed configuration and smaller than the deployed configuration, after displacement of the medical device from the deployment sheath. Maintaining the device at an intermediate state allows final positioning of the device at the treatment site prior to committing to a full deployment of the device.

The example medical device 140 is constructed from one or more components and sub-components. For example, the medical device 140 includes frame members 142, a covering 144, and an attachment feature 146. As used herein, "frame" may refer to an entire frame of a device, or may alternatively refer to a localized portion of a device that includes at least one elongate member. In addition, "frame" refers to various forms of frames, including, but not limited to, tubes, wires, and other suitable types of frames.

In this example embodiment, the medical device 140 is configured to self-expand when released from the confines of the deployment sheath 130 as a result of a bias or shape-memory property of the frame members 142. For example, the medical device 140 is shown in an expanded configuration, which is a result of the self-expanding nature of its frame members 142. Frame members 142 can be, for example, spring wires, shape memory alloy wires, or super-elastic alloy wires. Frame members 142 can be made of nitinol (NiTi), L605 steel, stainless steel, or any other appropriate biocompatible material. The super-elastic properties of NiTi make it a particularly good candidate material for such frame members 142 (e.g., NiTi wires can be heat-set into a desired shape). The frame members 142 may include one or more regions that can provide, for example, suitable positions for anchoring features, such as fixation anchors, barbs, protrusions, and the like that may be provided on the medical device 140.

Medical device 140 includes a covering 144 that, for example, inhibits or prevents passage of blood and other body fluids. In some embodiments, covering 144 is a thin flexible material. In some embodiments, the covering 144 has a microporous structure that provides a tissue ingrowth scaffold for durable occlusion and supplemental anchoring strength of the medical device 140. In some embodiments, the covering 144 comprises a fluoropolymer, such as an expanded polytetrafluoroethylene (ePTFE) polymer. In some embodiments, the covering 144 comprises Dacron, Bio A, or copolymers.

Figure 2B:
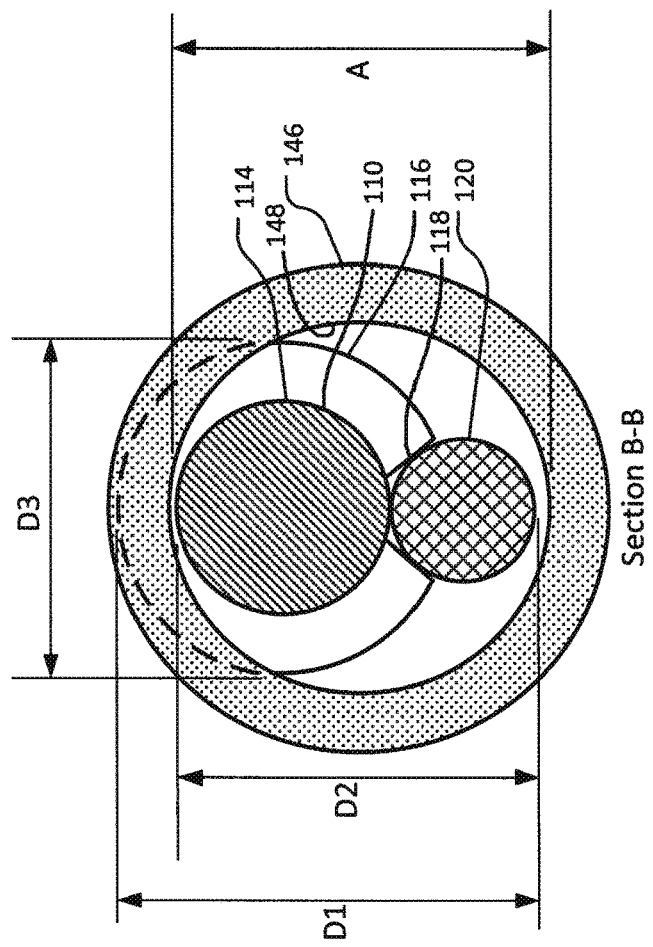
FIG. 2B is a cross-sectional view of the example deployment system of FIGS. 1A-1E coupled to the medical device in correspondence with FIG. 2A.

Medical device 140 includes an attachment feature 146 to which the body member 110 can be releasably coupleable. The attachment feature 146 can be used by the deployment system 100 to exert control over the medical device 140 during the deployment process. The control aspects can include, for example, the positioning and release of the medical device 140. In this example, the attachment feature 146 is a collar that is annular-shaped and defines an aperture 148, as best shown in FIG. 2B. In some other embodiments of medical devices, the end portions of one or more frame members can be coiled, looped, or twisted to form eyelets that can serve as attachment features (refer to FIGS. 8A-8C). In some embodiments, hubs, tubes, lumens, sleeves, and other structures that define an aperture can be used for an attachment feature of a medical device. In some embodiments, the aperture has a circular cross-sectional shape. In some embodiments, the aperture has a non-circular cross-sectional shape including, but not limited to, ovular, square, rectangular, triangular, and others.

The example medical device 140 includes a single attachment feature 146. Other embodiments of medical devices can include two or more attachment features, e.g., a distal eyelet and proximal eyelet, hubs, collars, and the like. The deployment systems and techniques provided herein can also be used to deploy medical devices that include such multiple attachment features (refer to FIGS. 9A-9D, 10A-10D, and 11A-11E). The example medical device 140 includes a single attachment feature 146 located at the proximal end of the medical device 140. In some other medical device embodiments, a single attachment feature is located near the distal end of the device. In still other medical device embodiments, a single attachment feature is located between the proximal and distal ends of the device. The deployment systems and techniques provided herein can also be used to deploy medical devices that have single attachment features located in any such positions, or positions therebetween.

When the medical device 140 is locked to the deployment device 100, the attachment feature 146 is located around the coupling portion 114 between the first and second enlarged portions 112, 116 of the body member 110, and the body locking member 120 protrudes at least partially through the aperture 148 defined by the attachment feature 146. In this configuration, the medical device 140 is coupled in a locked manner to the deployment system 100 such that the attachment feature 146 is retained between the first and second locking surfaces 113, 117 defined on the first and second enlarged portions 112, 116, respectively.

FIG. 2B is a cross-sectional view of the attachment feature 146 in its retained position on the coupling portion 114. The other components of the medical device 140 are not shown in this view so as to enhance the clarity of certain aspects of the illustration. As described in reference to FIG. 1E, the combination of the body member 110 and the body locking member 120 creates one or more physical dimensional aspects that are used advantageously by the deployment system 100 to releasably couple the medical device 140 with the deployment system 100.

The dimension A is the diameter of the aperture defined by the attachment feature 146. The dimension A is equal to or slightly larger than dimension D2 which is the maximum distance from the outer surface of the coupling portion 114 to the outer surface of the body locking member 120. As such, the attachment feature 146 can surround the combination of the body member 110 and the body locking member 120 when the attachment feature 140 is located at the coupling portion 114, and the body member 110 and the body locking member 120 are engaged with each other.

The dimension A is less than the dimension D1 which is the maximum distance between the outer surface of the second enlarged portion 116 and the outer surface of the body locking member 120. As such, the attachment feature 146 can be held on the coupling portion 114 and restrained from passing over the combination of the body locking member 120 and the second enlarged portion 116 and/or the first enlarged portion 112. By this arrangement, the attachment feature 146 is retained between the first and second locking surfaces 113, 117 defined on the first and second enlarged portions 112, 116 when the attachment feature 146 is located at the coupling portion 114; and when the body locking member 120 is engaged with the body member 110 and extends through the aperture 148 defined by the attachment feature 146.

However, the dimension A is greater than the dimension D3 which is the maximum outer dimension of the second enlarged portion 116. Therefore, when the body locking member 120 is removed from protruding through the attachment feature 146, the medical device 140 can become unlocked and decoupled from the deployment system 100. That is, with the body locking member 120 displaced from the aperture 148 defined by the attachment feature 146, and with the aperture 148 of the attachment feature 146 being larger than the dimension D3 of the second enlarged portion 116, the attachment feature 146 can be slid over second enlarged portion 116, and fully away from the body member 110 if desired. In this manner, the body locking member 120 can serve a locking function to keep the attachment feature 146 retained between the first and second enlarged portions 112 and 116 of the body member 110 when the body locking member 120 protrudes into the aperture 148 defined by the attachment feature 146. When the body locking member 120 is removed from protruding within the aperture 148 of the attachment feature 146, the attachment feature 146 is effectively unlocked from being retained between the first and second enlarged portions 112 and 116 of the body member 110.

FIGS. 2A and 2C-2E are a series of illustrations that depict the decoupling of the medical device 140 from the deployment system 100. That is, these figures generally depict the sequential operations that can be followed when the medical device 140 is deployed at a target delivery site in the body of a patient. As described previously, FIG. 2A shows the medical device 140 releasably locked to the deployment system 100.

FIG. 2C depicts the beginning of the process of unlocking and decoupling the medical device 140 from the deployment system 100. In this arrangement, the body locking member 120 has been displaced axially proximally to remove the body locking member 120 from protruding through the aperture (148 in FIG. 2B) defined by the attachment feature 146. The attachment feature 146 is therefore no longer locked to the body member 110 in this arrangement. In some embodiments, the body locking member 120 can be configured such that the medical device 140 can be unlocked from the deployment system 100 by moving the body locking member 120 distally.

FIG. 2D illustrates the partial retraction of the body member 110 away from the attachment feature 146 to further the process of decoupling the deployment system 100 from the medical device 140. With the body locking member 120 removed from protruding through the aperture (148 in FIG. 2B) of the attachment feature 146, the aperture defined by the attachment feature 146 can span the maximum outer dimension of the second enlarged portion 116 (dimension D3 of FIG. 2B). Therefore, physical clearance exists between the attachment feature 146 and the body member 110 such that they can be decoupled from each other.

FIG. 2E illustrates the full separation of the body member 110 and the attachment feature 146 to complete the process of decoupling the deployment system 100 and the medical device 140. The deployment sheath 130 containing the body member 110 and the body locking member 120 can now be retracted from the patient, while the medical device 140 remains in the patient's body.

FIGS. 3A-3E depict another example deployment system 300 including a body member 310 and a body locking member 320. It should be understood that the deployment system 300 also includes a deployment sheath (not shown) and, optionally, a deployment actuator. The construction and use of the deployment system 300 is generally analogous to the deployment system 100 described above.

While deployment system 300 has many similarities with deployment system 100, a few differences exist between exemplary deployment systems 100 and 300. For example, body member 310 includes a flat surface 318. In some embodiments, the flat surface 318 is on the entire length of the body member 310, including the nominal diameter portions and the regions of the first and second enlarged portions 312 and 316. In some embodiments, the flat surface 318 is only on the regions of the first and second enlarged portions 312 and 316. The flat surface 318, like the groove 118 (refer to FIGS. 1A-1E), can mitigate some potential for undesirable twisting of the body member 310 with the body locking member 320, which could inhibit their axial movements relative to each other. In some embodiments, one or both of the body member 310 or the body locking member 320 can include one or more collars or sleeves through which the other of the body member 310 or the body locking member 320 passes. The use of such collars or sleeves can provide additional resistance against twisting.

Figure 3A:
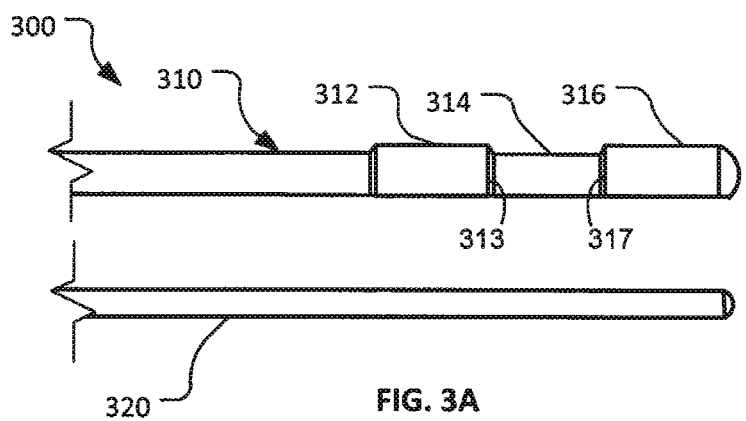
FIG. 3A depicts the distal end portions of another example deployment system, in accordance with some embodiments.
Figure 3B:
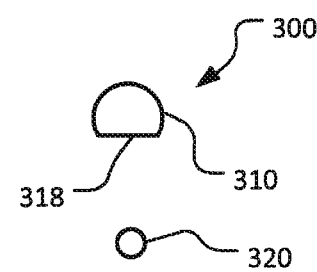
FIG. 3B illustrates an end view of the distal end portions of the deployment system of FIG. 3A.
Figure 3C:
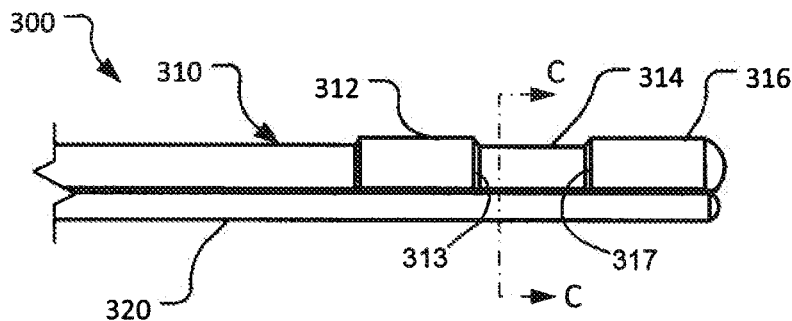
FIG. 3C illustrates the distal end portions of the deployment system of FIG. 3A in an engaged configuration.
Figure 3D:
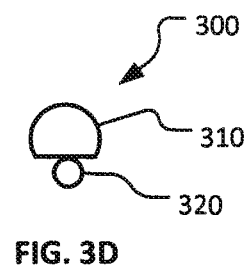
FIG. 3D illustrates an end view of the engaged distal end portions of the deployment system in correspondence with FIG. 3C.
Figure 3E:
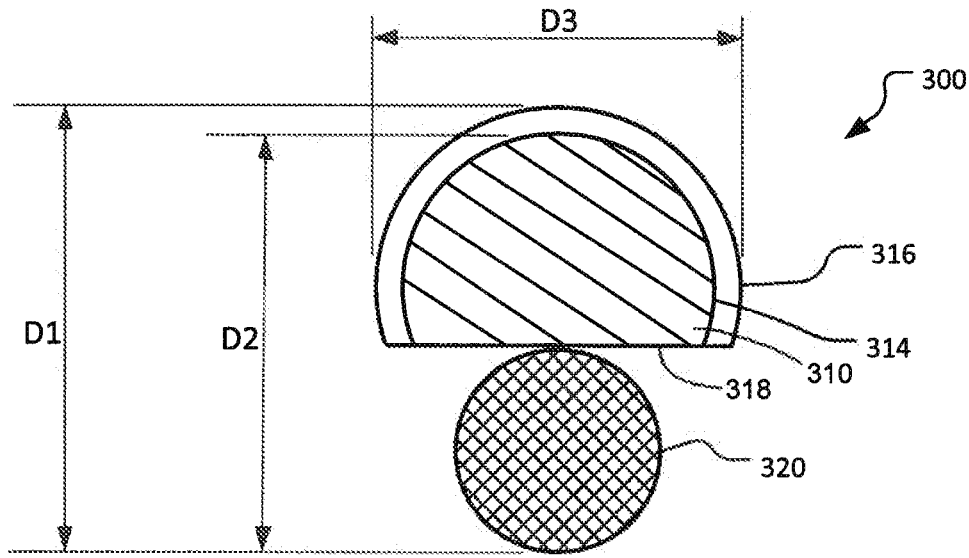
FIG. 3E is a cross-sectional view of the engaged distal end portions of the deployment system of FIG. 3C.

As shown in FIG. 3E, the physical dimensional aspects used to lock an attachment feature of a medical device to the deployment system 300 are similar to those of deployment system 100. As with deployment system 100, an aperture of a medical device attachment feature (not shown) will be equal to or slightly larger than D2; smaller than D1; and larger than D3. With such dimensional relationships, the deployment system 300 will be able to retain an attachment feature of a medical device (not shown) between the first and second locking surfaces 313, 317 of the first and second enlarged portions 312 and 316, respectively, when the attachment feature is on the coupling portion 314 and the body locking member 320 is cooperatively engaged with the body member 310 such that the body locking member 320 protrudes through the aperture. When the body locking member 320 is retracted so that it no longer protrudes through the aperture of the attachment feature, then the medical device can be decoupled from the deployment system 300.

FIGS. 4A-4E depict another example deployment system 400 including a body member 410 and a body locking member 420. It should be understood that the deployment system 400 also includes a deployment sheath (not shown) and, optionally, a deployment actuator. The construction and use of the deployment system 400 is generally analogous to the deployment systems 100 and 300 described previously.

While deployment system 400 has many similarities with deployment systems 100 and 300, a few differences exist. For example, neither the body member 410 nor the body locking member 420 includes surface features by which the body member 410 and body locking member 420 cooperatively engage with each other. Rather, the rounded outer surfaces of the body member 410 and body locking member 420 merely contact each other. In some embodiments, one or both of the body member 410 or the body locking member 420 can include one or more collars or sleeves 422 through which the other of the body member 410 or the body locking member 420 passes. The use of such collars or sleeves 422 can provide resistance against the twisting of the body member 410 with the body locking member 420.

The body member 410 includes a first protrusion 412 and a second protrusion 416. These protrusions 412 and 416 can be formed, for example, by grinding, or by welding, gluing, or over-molding additional material to the nominal diameter portion of the body member 410.

As shown in FIG. 4E, in some embodiments the dimensional aspects used to lock an attachment feature of a medical device to the deployment system 400 are similar to those of deployment systems 100 and 300. As with deployment systems 100 and 300, an aperture defined by an attachment feature (not shown) will be equal to or slightly larger than D2; smaller than D1; and larger than D3. With such dimensional relationships, the deployment system 400 will be able to retain an attachment feature of a medical device between the first and second locking surfaces 413, 417 of the first and second enlarged portions 412 and 416, respectively, when the attachment feature is on the coupling portion 414 and the body locking member 420 protrudes into or through the aperture. When the body locking member 420 is retracted so that it no longer protrudes into the aperture of the attachment feature, then the medical device can be decoupled from the deployment system 400.

FIGS. 5A-5C are a series of illustrations depicting the deployment of medical device 140 using another example deployment system 500. The deployment system 500 includes a deployment sheath 130 that is used to transmit to a target delivery site a body member 510 and a body locking member 520. In this embodiment, the body locking member 520 is at least partially located in a lumen 511 defined by the body member 510. However, a distal end 521 of the body locking member 520 can emerge from the lumen 511 of the body member 510 and protrude through the aperture (not shown) defined by the attachment feature 146 of the medical device 140, so as to lock the medical device 140 to the body member 510.

In the region of the coupling portion 514 and the attachment feature 146, the body member 510 and the body locking member 520 function as described by deployment systems 100, 300, and 400. That is, the dimensional relationships defined by the body member 510, the body locking member 520, and the aperture of the attachment feature 146 enable the deployment system 500 to retain or lock the attachment feature 146 between the first and second locking surfaces 513, 517 of the first and second enlarged portions 512 and 516, respectively, when the attachment feature 146 is on the coupling portion 514 and the body locking member 520 protrudes into or through the aperture. When the body locking member 520 is retracted so that it no longer protrudes into the aperture of the attachment feature 146, then the medical device 140 can be decoupled from the deployment system 500. The first and second enlarged portions 512 and 516 can be configured like any of the enlarged portions described herein.

FIGS. 6A-6C are a series of illustrations depicting the deployment of medical device 140 using another example deployment system 600. The deployment system 600 includes a deployment sheath 130 that is used to transmit to a target delivery site a body member 610 and a body locking member 620 that are coupled and locked to the medical device 140. In some embodiments, the body locking member 620 is at least partially located in and selectively axially displaceable along a lumen 611 defined by the body member 610. However, the distal end 621 of the body locking member 620 can emerge from the lumen 611 of the body member 610 and protrude into or through the aperture 148 defined by the attachment feature 146 of the medical device 140, so as to lock the medical device 140 to the body member 610.

The body member 610 of deployment system 600 comprises a catheter shaft 612 with a distal extension comprising a coupling portion 614 that has a bulbous tip 616. The catheter shaft 612 defines the lumen 611 that can movably contain the body locking member 620. In some embodiments, the coupling portion 614 is fixedly attached to the distal end of the catheter shaft 612 of the body member 610. In other embodiments, the coupling portion can be movable in relation to the catheter shaft. The bulbous tip 616 is fixedly attached to the distal tip of the coupling portion 614. In some embodiments, the bulbous tip 616 is centered with the axis of the coupling portion 614. In some embodiments, the bulbous tip 616 is off-set from the axis of the coupling portion 614. The bulbous tip 616 can be a variety of shapes including, but not limited to, spherical, conical, tapered, ovular, irregular, and a cube or another polyhedron. In some embodiments, the bulbous tip 616 is formed on the end of the coupling portion 614 using laser energy to deform the tip of the coupling portion 614 into a bulbous shape. In some embodiments, the bulbous tip 616 is originally a separate component that gets attached to the tip of the coupling portion 614 by welding, gluing, over-molding, casting, crimping, press-fitting, and the like.

In FIG. 6A, the medical device 140 is coupled and locked to the deployment system 600 because the attachment feature 146 is on the coupling portion 614 and the body locking member 620 is protruding through the aperture 148 of the attachment feature 146. The inner diameter ("ID") of the aperture defined by the attachment feature 146 is smaller than the outer diameter ("OD") of the catheter shaft 612 and smaller than the dimension defined by the combination of the bulbous tip 616 and the body locking member 620. Therefore, the attachment feature 146 is retained on the coupling portion 614 between the catheter shaft 612 and the bulbous tip 616.

In FIG. 6B, the body locking member 620 has been retracted such that the body locking member 620 no longer protrudes into the aperture 148 of the attachment feature 146. As such, the medical device 140 is no longer locked on the body member 610. FIG. 6C shows the deployment system 600 after the body member 610 has been retracted from the attachment feature 146 such that the medical device 140 is fully decoupled from the deployment system 600. The deployment sheath 130 containing the body member 610 and the body locking member 620 can now be retracted from the patient, while the medical device 140 remains in the patient's body.

FIGS. 7A-7C are a series of illustrations depicting the deployment of a medical device 740 using another example deployment system 700. The medical device 740 is an example stent device. The deployment system 700 includes a deployment sheath 130 that is used to transmit to a target delivery site a body member 710 (illustrated with a cut-away at the distal tip) and a body locking member 720 that are coupled and locked to the medical device 740. In some embodiments, the body locking member 720 is at least partially located in a lumen 711 defined by a catheter shaft 712 of the body member 710. However, a distal end 721 of the body locking member 720 can protrude from the body member 710 and into or through an aperture 716 at the distal tip of the catheter shaft 712. The body locking member 720 can protrude into or through the aperture 716 of the catheter shaft 712, so as to lock the medical device 740 to the body member 710.

As shown in FIG. 7C, the medical device 740 includes an attachment feature 746. The attachment feature 746 includes a fixedly attached extension 747 with a bulbous tip 748. The bulbous tip 748 can be a variety of shapes including, but not limited to, spherical, conical, tapered, ovular, irregular, and a cube or another polyhedron. In some embodiments, the bulbous tip 748 is formed on the end of the extension 747 using laser energy to deform the tip of the extension 747 into a bulbous shape. In some embodiments, the bulbous tip 748 is originally a separate component that gets attached to the tip of the extension 747 by welding, gluing, over-molding, casting, crimping, press-fitting, and the like. When the medical device 740 is coupled to the deployment system 700, the bulbous tip 748 protrudes through the aperture 716 and the body locking member 720 is extended at least into the aperture 716 (refer to FIG. 7A). The dimensional relationships defined by the bulbous tip 748, the body locking member 720, and the aperture 716 allow the deployment system 700 to retain the attachment feature 746 to the body member 710 when the bulbous tip 748 protrudes through the aperture 716 and the body locking member 720 protrudes into the aperture 716. When the body locking member 720 is retracted so that the body locking member 720 no longer protrudes into the aperture 716, then the medical device 740 is unlocked from and can be decoupled from the deployment system 700.

Figure 8A:
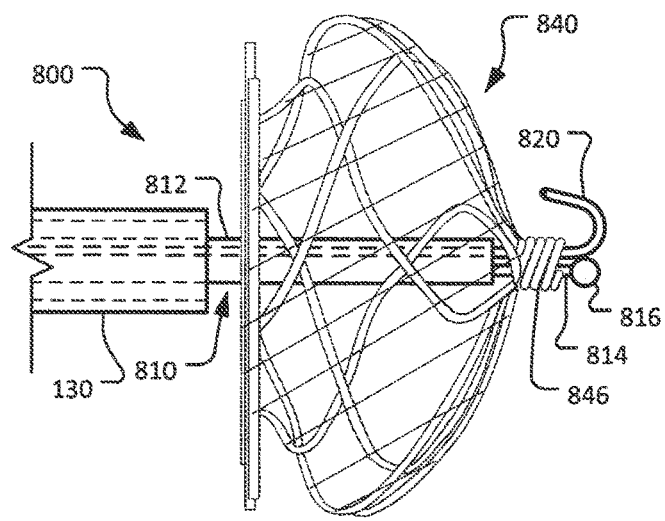
FIGS. 8A-8C are a series of illustrations depicting the deployment of a medical device using another example deployment system.
Figure 8B:
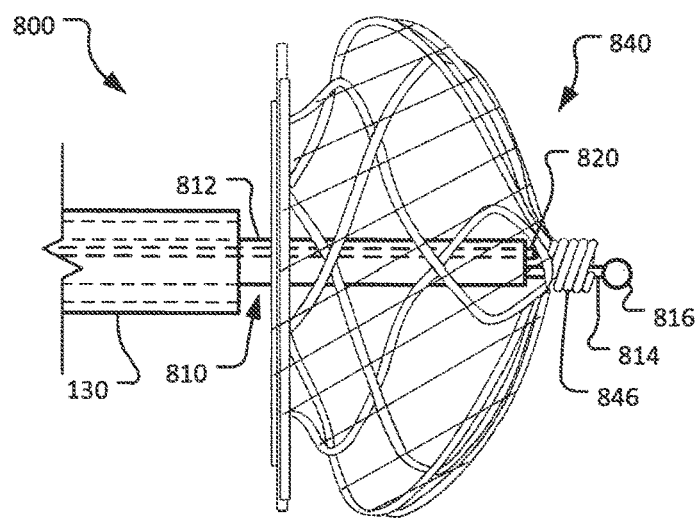
Figure 8C:
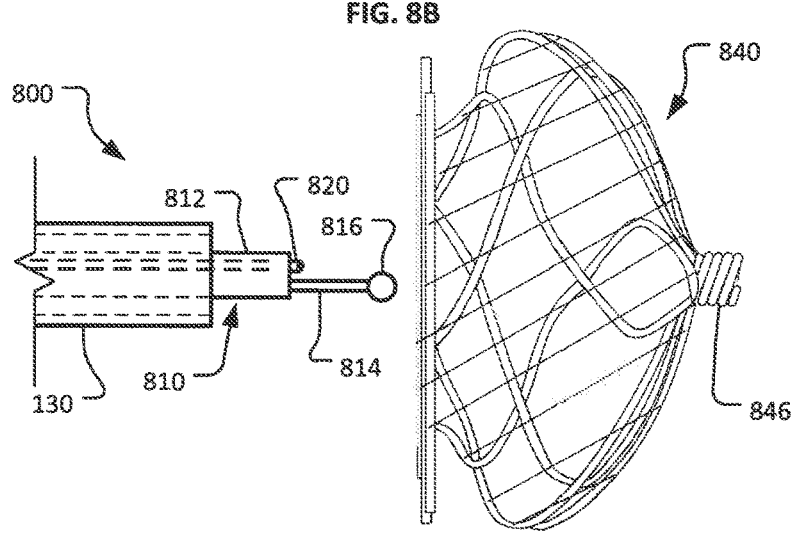

FIGS. 8A-8C are a series of illustrations depicting the deployment of a medical device 840 using another example deployment system 800. The medical device 840 is an example of a medical device that has an attachment feature 846 at the distal end of the medical device 840. In this example, the attachment feature 846 is a coil of frame member terminations that define an aperture. In some embodiments, various other types of attachment features can be included while keeping the structure and functionality of the deployment system 800 essentially unchanged.

The deployment system 800 includes a deployment sheath 130 that is used to transmit to a target delivery site a body member 810 and a body locking member 820, such that the body member 810 is coupled and locked to the medical device 840. In some embodiments, the body locking member 820 is at least partially located in a lumen defined by a catheter shaft 812 of the body member 810. However, in some embodiments the distal end of the body locking member 820 can exit from the lumen of the catheter shaft 812 and protrude into or through the aperture defined by the attachment feature 846 of the medical device 840, so as to lock the medical device 840 to the body member 810 when the attachment feature 846 is on a coupling position 814. In some embodiments, the distal end of the body locking member 820 includes an atraumatic tip (a blunt or bulbous tip having a variety of shapes including, but not limited to, radiused, beveled, spherical, conical, tapered, ovular, irregular, and polyhedron) that can be included to reduce the potential for inflicting tissue damage as compared to certain other tip designs. As described previously, the body locking member 820 can be flexible and, in some embodiments, super-elastic. Therefore, as the locking body member is retracted, the distal bent portion will become substantially straightened as it comes into contact with the attachment feature 846 and the lumen of the catheter shaft 812.

The body member 810 of deployment system 800 comprises the catheter shaft 812 with a distal extension comprising the fixedly attached coupling portion 814 that has a bulbous tip 816. The catheter shaft 812 defines a lumen that can movably contain the body locking member 820. In some embodiments, the coupling portion 814 is fixedly attached to the distal end of the catheter shaft 812 of the body member 810. In some embodiments, the coupling portion can be movable in relation to the catheter shaft 812. The bulbous tip 816 is fixedly attached to the distal tip of the coupling portion 814. In some embodiments, the bulbous tip 816 is centered with the axis of the coupling portion 814. In some embodiments, the bulbous tip 816 is off-set from the axis of the coupling portion 814. The bulbous tip 816 can be a variety of shapes including, but not limited to, spherical, ovular, irregular, and a cube or another polyhedron. In some embodiments, the bulbous tip 816 can have an atraumatic configuration (a blunt or bulbous tip having a variety of shapes including, but not limited to, radiused, beveled, spherical, conical, tapered, ovular, irregular, and polyhedron). In some embodiments, the bulbous tip 816 is formed on the end of the coupling portion 814 using laser energy to deform the tip of the coupling portion 814 into a bulbous shape. In some embodiments, the bulbous tip 816 is originally a separate component part that gets attached to the tip of the coupling portion 814 by welding, gluing, over-molding, casting, crimping, press-fitting, and the like.

In FIG. 8A, the medical device 840 is coupled and locked to the deployment system 800 because the attachment feature 846 is on the coupling portion 814 and the body locking member 820 is protruding through the aperture of the attachment feature 846. The ID of the aperture of the attachment feature 846 is smaller than the outer diameter OD of the catheter shaft 812 and smaller than the dimension defined by the combination of the bulbous tip 816 and the body locking member 820. Therefore, the attachment feature 846 is retained on the coupling portion 814 between the catheter shaft 812 and the bulbous tip 816.

In FIG. 8B, the body locking member 820 has been retracted such that the body locking member 820 no longer protrudes into the aperture defined by the attachment feature 846. As such, the medical device 840 is no longer locked on the body member 810. FIG. 8C shows the body member 810 after being retracted from the attachment feature 846 such that the medical device 840 is fully decoupled from the deployment system 800. The deployment sheath 130 containing the body member 810 and the body locking member 820 can now be retracted from the patient, while the medical device 840 remains in the patient's body.

FIGS. 9A-9D, 10A-10D, and 11A-11E illustrate deployment systems and techniques for deploying medical devices that have two or more attachment features. In order to enhance the clarity of the figures, only the example attachment features of the medical devices are illustrated. That is, the portions of the example medical devices other than the example attachment features are not shown so that the deployment systems and techniques are clearly visible. In addition, those attachment features are shown in cross-section so that the inside of the attachment features can be visualized. While these figures include particular types of deployment system components (e.g., body members and body locking members), it should be understood that the type of deployment system components used for these deployment systems can include any of the previously explained embodiments, and combinations or sub-combinations of those embodiments and equivalents to those embodiments.

FIGS. 9A-9D are a series of illustrations depicting a deployment system 900 that is performing the deployment of a medical device (not shown) that has a first attachment feature 946 and a second attachment feature 956. In general, during deployment, the deployment system 900 first unlocks from the second attachment feature 956 and subsequently unlocks from the first attachment feature 946.

The deployment system 900 includes a body member 910, a body locking member 920, a deployment sheath (not shown), and, optionally, a deployment actuator (not shown). The body member 910 includes a first coupling region 911 and a second coupling region 915. The first coupling region 911 includes a first enlarged portion 912, a first coupling portion 913, and a second enlarged portion 914. The second coupling region 915 includes a third enlarged portion 916, a second coupling portion 917, and a fourth enlarged portion 918.

The first attachment feature 946 is locked to the first coupling portion 913 and the second attachment feature 956 is locked to the second coupling portion 917 when the body locking member 920 protrudes into or through apertures 948, 958 defined by the attachment features 946 and 956. That is the case because, similarly with previously described embodiments, the aperture 948 defined by the first attachment feature 946 is smaller than the dimension defined by the combination of the body locking member 920 and the enlarged portions 912 or 914, and the aperture 958 defined by the second attachment feature 956 is smaller than the dimension defined by the combination of the body locking member 920 and the enlarged portions 916 or 918.

Figure 9A:
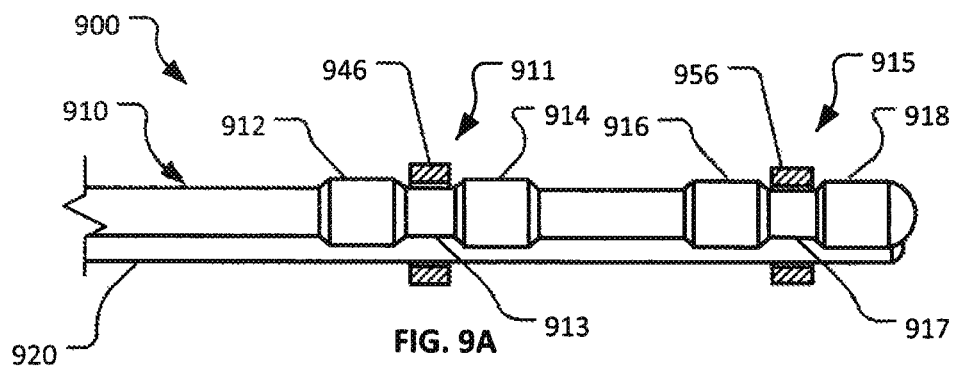
FIGS. 9A-9D are a series of illustrations depicting the deployment of a medical device using another example deployment system.
Figure 9B:
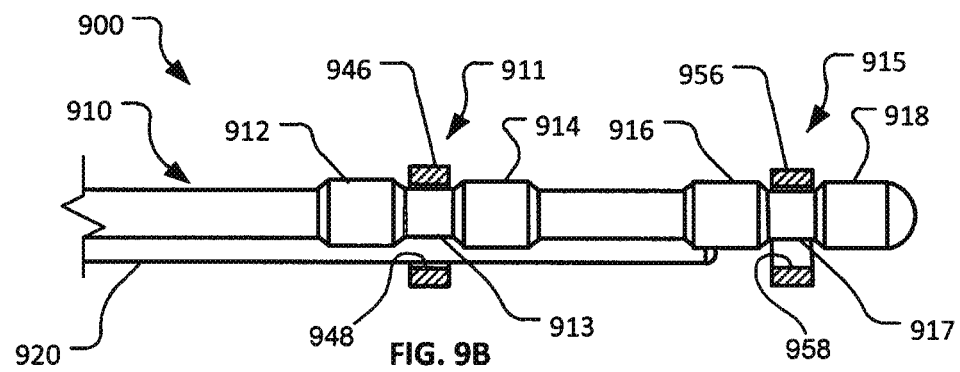
Figure 9C:
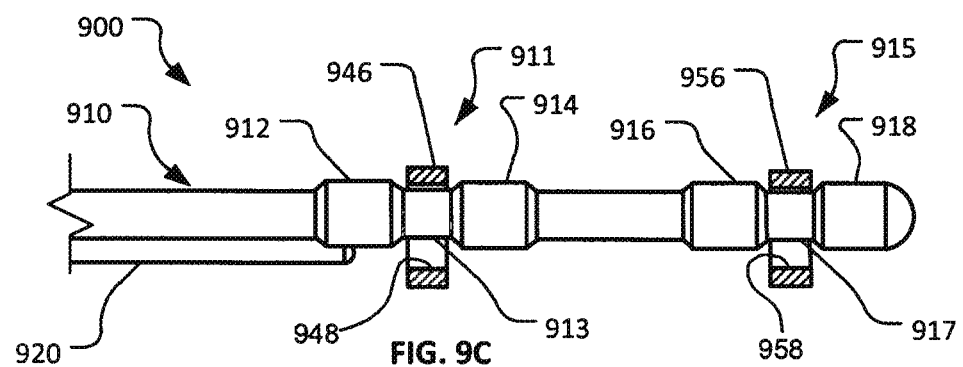
Figure 9D:
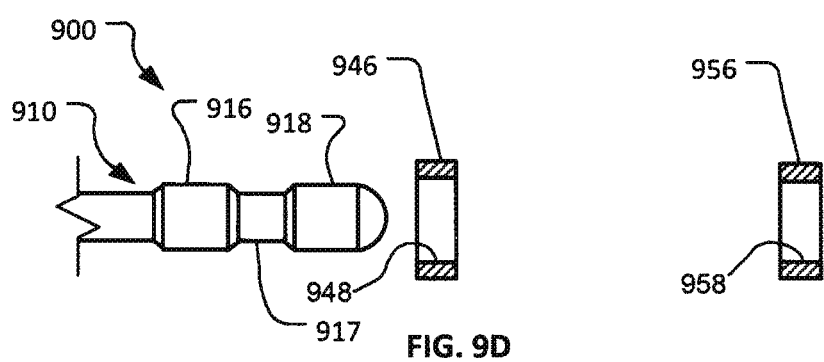

To begin the process of decoupling the medical device from the deployment system 900, the clinician operator can begin retracting the body locking member 920 in relation to the body member 910. As shown in FIG. 9B, the body locking member 920 will first be retracted such that the body locking member 920 no longer protrudes through the aperture 958 of the second attachment feature 956. In that particular arrangement, the second attachment feature 956 is no longer locked to the body member 910 (although the body member 910 is still protruding through the aperture 958 defined by the second attachment feature 956). As the clinician continues retracting the body locking member 920, the body locking member 920 will eventually no longer protrude into the aperture 948 defined by the first attachment feature 946 (refer to FIG. 9C). In that arrangement, neither of the first nor second attachment features 946 and 956 are any longer locked to the body member 910 (although the body member 910 is still protruding through the apertures 948, 958 defined by the first and second attachment features 946 and 956). Next, the body member 910 can be retracted by the clinician operator such that it is no longer protruding through the apertures 948, 958 of the first and second attachment features 946 and 956 (refer to FIG. 9D). At this stage, the medical device is fully decoupled from the deployment system 900, and deployment sheath containing the body member 910 and the body locking member 920 can now be retracted from the patient, while the medical device remains in the patient's body.

FIGS. 10A-10D are a series of illustrations depicting a deployment system 1000 that is performing the deployment of a medical device that has a first attachment feature 1046 and a second attachment feature 1056. In this embodiment, the first attachment feature 1046 defines a larger aperture than the second attachment feature 1056. In general, during deployment, the deployment system 1000 first unlocks from the first attachment feature 1046 and subsequently unlocks from the second attachment feature 1056. This sequence is the reverse of the deployment system 900 described above.

The deployment system 1000 includes a body member 1010, a body locking member 1020, a deployment sheath (not shown), and, optionally, a deployment actuator (not shown). The body member 1010 includes a first coupling region 1011 and a second coupling region 1015. The first coupling region 1011 includes a first enlarged portion 1012, a first coupling portion 1013, and a second enlarged portion 1014. The second coupling region 1015 includes a third enlarged portion 1016, a second coupling portion 1017, and a fourth enlarged portion 1018.

The body locking member 1020 includes a first portion 1022 and a second portion 1024. The first portion 1022 includes a physical feature that makes the profile different (e.g., larger) than the second portion 1024. In some embodiments, the physical feature is a rib, a protrusion, a step, a land, and the like. Such features can result from the process of forming the body locking member 1020 by grinding, or by the attachment of one or more separate components onto the body locking member 1020 by welding, gluing, press-fitting, crimping, and the like. The first portion 1022 of the body locking member 1020 protrudes into or through the first attachment feature 1046, but not into or through the second attachment feature 1056. The second portion 1024 of the body locking member 1020 protrudes into or through the second attachment feature 1056.

The first attachment feature 1046 is locked to the first coupling portion 1013, and the second attachment feature 1056 is locked to the second coupling portion 1017, when the body locking member 1020 protrudes through the apertures defined by the attachment features 1046 and 1056. That is the case because, similarly with previously described embodiments, the aperture defined by the first attachment feature 1046 is smaller than the dimension defined by the combination of the first portion 1022 of the body locking member 1020 and the enlarged portions 1012 or 1014, and the aperture defined by the second attachment feature 1056 is smaller than the dimension defined by the combination of the second portion 1024 of the body locking member 1020 and the enlarged portions 1016 or 1018.

Figure 10A:
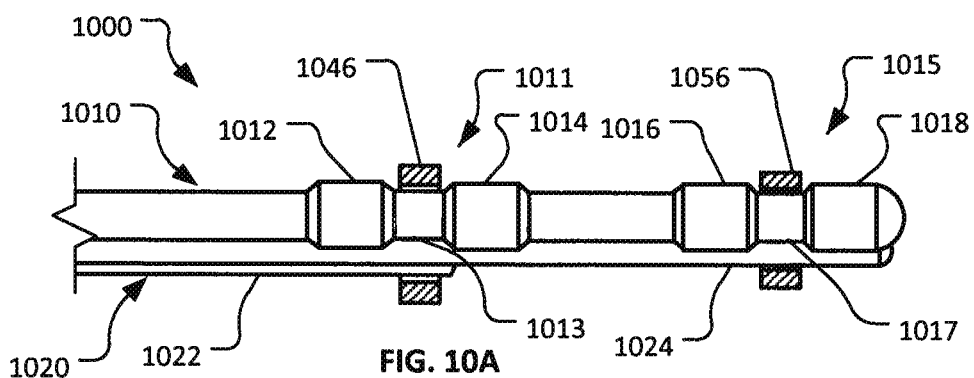
FIGS. 10A-10D are a series of illustrations depicting the deployment of a medical device using another example deployment system.
Figure 10B:
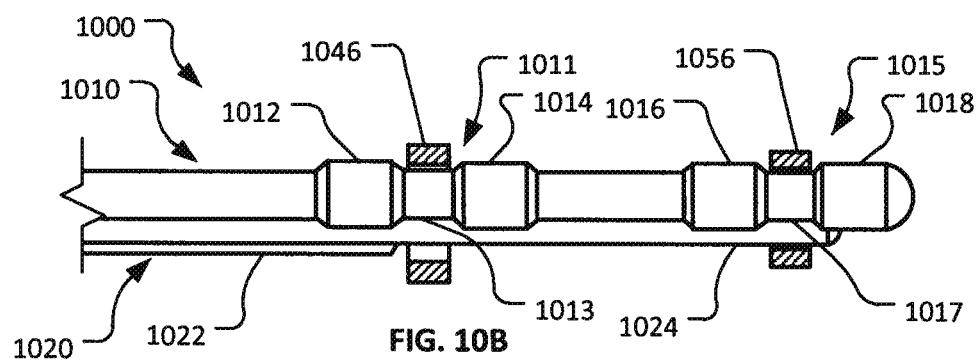
Figure 10C:
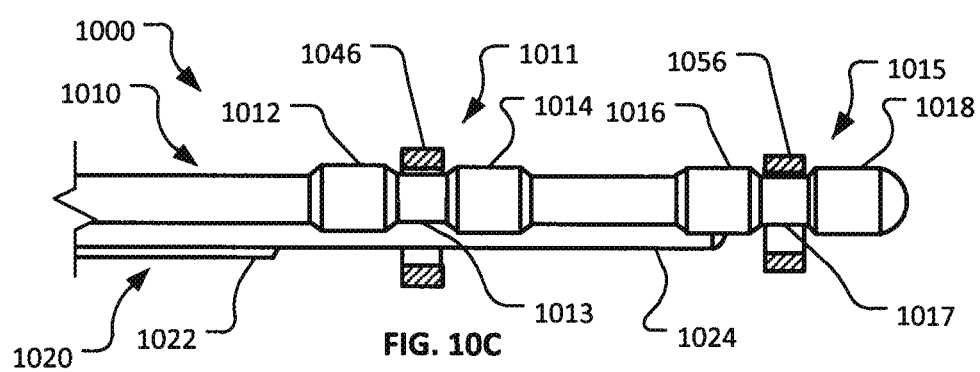
Figure 10D:
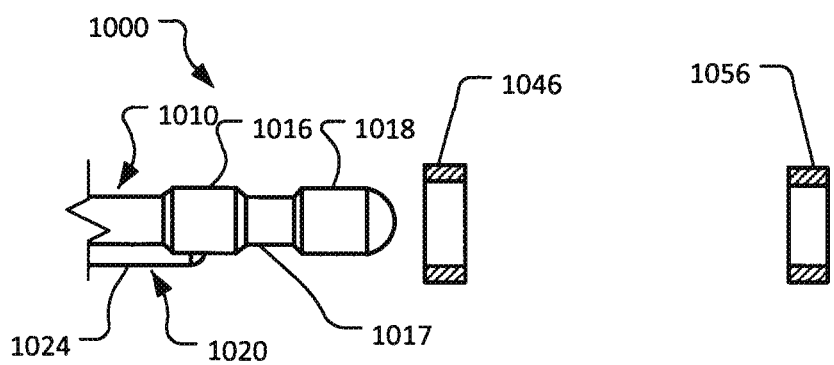

To begin the process of decoupling the medical device from the deployment system 1000, the clinician operator can begin to retract the body locking member 1020 in relation to the body member 1010. As shown in FIG. 10B, the body locking member 1020 will first be retracted such that the first portion 1022 no longer protrudes into the aperture defined by the first attachment feature 1046. In that arrangement, the first attachment feature 1046 is no longer locked to the body member 1010 (although the body member 1010 is still protruding through the aperture defined by the first attachment feature 1046). As the clinician continues retracting the body locking member 1020, second portion 1024 of the body locking member 1020 will eventually no longer protrude into the aperture defined by the second attachment feature 1056 (refer to FIG. 10C). In that arrangement, neither the first nor second attachment features 1046 and 1056 are any longer locked to the body member 1010 (although the body member 1010 is still protruding through the apertures defined by the first and second attachment features 1046 and 1056). Next, the body member 1010 can be retracted by the clinician operator such that it is no longer protruding through the apertures of the first and second attachment features 1046 and 1056 (refer to FIG. 10D). At this stage, the medical device is fully decoupled from the deployment system 1000, and deployment sheath containing the body member 1010 and the body locking member 1020 can now be retracted from the patient, while the medical device remains in the patient's body.

FIGS. 11A-11E are a series of illustrations depicting a deployment system 1100 that is performing the deployment of a medical device that has a first attachment feature 1146 and a second attachment feature 1156. In some embodiments, the first attachment feature 1146 has a larger aperture than the second attachment feature 1156. Deployment system 1100 illustrates how the operational principles of the deployment systems provided herein can be applied for use with medical device embodiments that have multiple attachment features. While deployment system 1100 depicts the deployment of a medical device with two attachment features, it should be understood that the same concepts can be applied to medical devices with three or more attachment features.

In this embodiment of an example medical device and deployment system 1100, the first and second attachment features 1146 and 1156 are movable in relation to each other while the attachment features 1146 and 1156 are coupled and locked to the deployment system 1100. Such an ability to facilitate movement between the attachment features 1146 and 1156 can be advantageous in conjunction with certain embodiments of medical devices. For example, some embodiments of medical devices can be stretched to thereby reconfigure the device to a low-profile delivery configuration for placement within a deployment sheath. Such stretching can, in some embodiments, be performed by extending the distance between the attachment features 1146 and 1156. Upon emergence of the medical device from the deployment sheath, the attachment features 1146 and 1156 can move closer to each other to allow the device to expand to a configuration for implantation. In general, during deployment, the deployment system 1100 first unlocks from the second attachment feature 1156 and subsequently unlocks from the first attachment feature 1146.

The deployment system 1100 includes a first body member 1110, a body locking member 1120, a second body member 1130, a deployment sheath (not shown), and, optionally, a deployment actuator (not shown). The first body member 1110 includes a first enlarged portion 1112, a first coupling portion 1114, and a second enlarged portion 1116. The second body member 1130 includes a third enlarged portion 1132, a second coupling portion 1134, and a fourth enlarged portion 1136.

The first attachment feature 1146 is locked to the first coupling portion 1114, and the second attachment feature 1156 is locked to the second coupling portion 1134, when the body locking member 1120 protrudes into or through the apertures defined by the attachment features 1146 and 1156. That is the case because, similarly with previously described embodiments, the aperture defined by the first attachment feature 1146 is smaller than the dimension defined by the combination of (i) the body locking member 1120, (ii) the nominal diameter of the second body member 1130, and (iii) the enlarged portions 1112 or 1114; and the aperture defined by the second attachment feature 1156 is smaller than the dimension defined by the combination of (i) the body locking member 1120 and (ii) the enlarged portions 1132 or 1136.

Figure 11A:
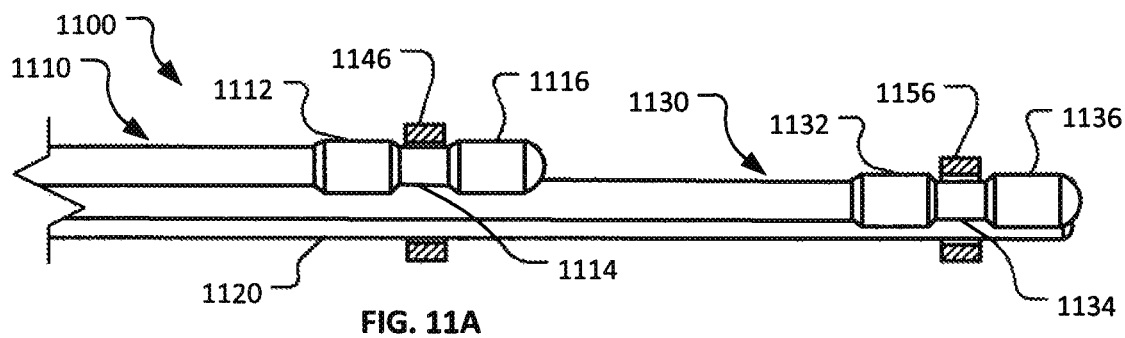
FIGS. 11A-11E are a series of illustrations depicting the deployment of a medical device using another example deployment system.
Figure 11B:
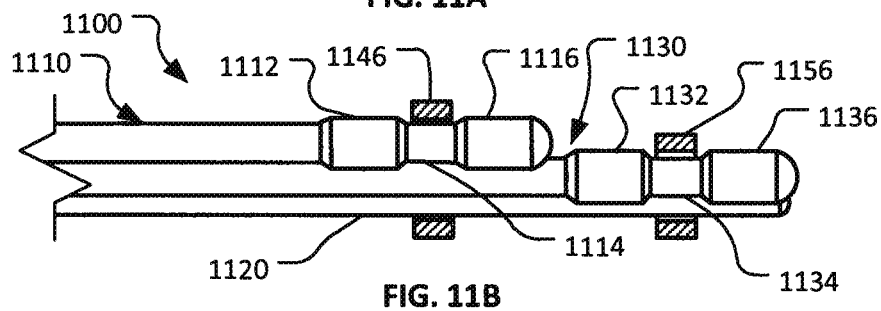
Figure 11C:
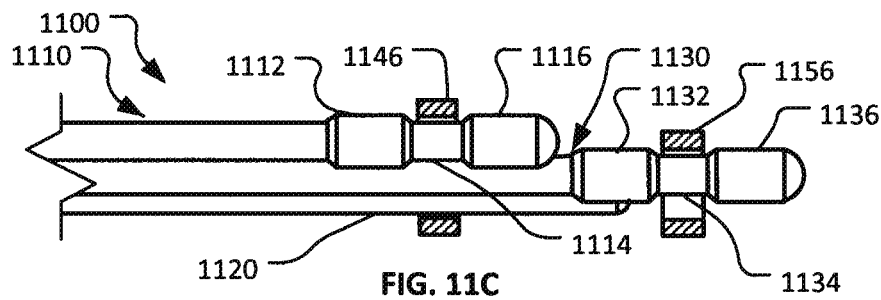
Figure 11D:
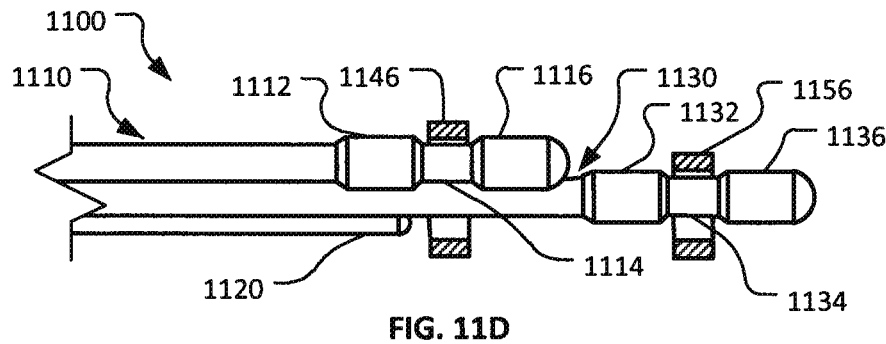
Figure 11E:
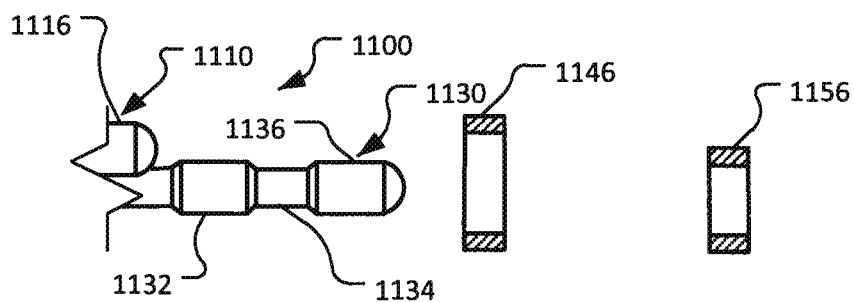

To begin the process of decoupling the medical device from the deployment system 1100, the clinician operator can begin retracting the body locking member 1120 in relation to the body members 1110 and 1130. As shown in FIG. 11C, the body locking member 1120 will first be retracted such that the body locking member 1120 no longer protrudes into the aperture defined by the second attachment feature 1156. In that arrangement, the second attachment feature 1156 is no longer locked to the body member 1130 (although the body member 1130 is still protruding through the aperture defined by the second attachment feature 1156). As the clinician continues retracting the body locking member 1120, the body locking member 1120 will eventually no longer protrude into the aperture defined by the first attachment feature 1146 (refer to FIG. 11D). In that arrangement, neither of the first nor second attachment features 1146 and 1156 are any longer locked to the body members 1110 and 1130 (although the body members 1110 and 1130 are still protruding through the apertures defined by the first and second attachment features 1146 and 1156 respectively). Next, the body members 1110 and 1130 can be retracted by the clinician operator such that the body members 1110 and 1130 are no longer protruding through the apertures of the first and second attachment features 1146 and 1156 (refer to FIG. 11E). At this stage, the medical device is fully decoupled from the deployment system 1100, and deployment sheath containing the body members 1110 and 1130 and the body locking member 1120 can now be retracted from the patient, while the medical device remains in the patient's body.

Additional examples of medical devices that can use the deployment systems and techniques provided herein are provided in the provisional patent application titled "Space Filling Devices," having inventors Coby C. Larsen, Brandon A. Lurie, Steven J. Masters, Thomas R. McDaniel, and Stanislaw L. Zukowski, filed on 16 Nov. 2012, assigned U.S. Ser. No. 61/727,458, and the provisional patent application titled "Space Filling Devices," having inventors Coby C. Larsen, Brandon A. Lurie, Steven J. Masters, Thomas R. McDaniel, and Stanislaw L. Zukowski, filed on 15 Mar. 2013, the disclosures of which are considered part of and are specifically incorporated by reference in their entirety (including the figures) for all purposes in the present disclosure.

For further additional examples of medical devices that can use the deployment systems and techniques described herein, see the provisional patent application titled "Joint Assembly for Medical Devices," having inventors Coby C. Larsen, Steven J. Masters, and Thomas R. McDaniel, filed on 16 Nov. 2012, assigned U.S. Ser. No. 61/727,328, and the non-provisional patent application titled "Joint Assembly for Medical Devices," having inventors Coby C. Larsen, Steven J. Masters, and Thomas R. McDaniel, filed on 15 Mar. 2013, the disclosures of which are considered part of and are specifically incorporated by reference in their entirety (including the figures) for all purposes in the present disclosure.

While this specification contains many specific implementation details, these should not be construed as limitations on the scope of any devices, methods, and systems discussed herein, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Particular embodiments of the subject matter have been described. Other embodiments are within the scope of the following claims.

What is claimed is:

1. A delivery system having a locked configuration and an unlocked configuration, the delivery system comprising:
   a medical device having an attachment feature arranged at an end of the medical device and frame members extending outwardly from the attachment feature relative to a longitudinal axis of the medical device, wherein the attachment feature has a diameter and maintains the same diameter in the locked configuration and the unlocked configuration;

a body member having a nominal diameter, a distal end portion, and a proximal end, wherein the distal end portion of the body member has enlarged portions including a proximal enlarged portion and a distal enlarged portion having increased diameters from the nominal diameter of a proximal section of the body member proximal to the proximal enlarged portion and a coupling portion, respectively, and cylindrical shapes extending at least partially circumferentially about the body member and the coupling portion of the body member is approximately equal in length to at least one of the enlarged portions;

a groove defined on an outer surface of the body member; and a body locking member having a nominal diameter, a distal end and a proximal end, the body locking member being configured to cooperatively engage along at least the distal end portion of the body member to releasably couple the body member to the medical device, and in the locked configuration, the body member is arranged through the attachment feature of the medical device while the groove engages and receives the body locking member with the enlarged portions being arranged on either side of the attachment feature to retain the medical device coupled to the body member, and to transition to the unlocked configuration, the body locking member is configured to slide longitudinally along the body member to allow a distal one of the enlarged portions of the body member to pass through the attachment feature of the medical device to uncouple the medical device from the body member, wherein the attachment feature defines an aperture with an inner diameter, wherein the inner diameter of the attachment feature is less than a combined diameter of the body locking member and the enlarged portions when the body locking member is cooperatively engaged along at least the distal end portion of the body member, and wherein the inner diameter of the attachment feature is greater than the combined diameter of the body locking member and the nominal diameter of the body member when the body locking member is cooperatively engaged along at least the distal end portion of the body member.

2. The delivery system of claim 1, wherein the inner diameter of the attachment feature is greater than a diameter of the enlarged portions.

3. The delivery system of claim 2, wherein the proximal enlarged portion and the distal enlarged portion are spaced apart from each other by a distance to thereby define the coupling portion of the body member that is configured to releasably couple with the attachment feature, the coupling portion of the body member having the nominal diameter.

4. The delivery system of claim 3, wherein one or both of the body member and the body locking member are comprised of a super-elastic metallic material.

5. The delivery system of claim 3, wherein one or both of the body member and the body locking member are comprised of nitinol.

6. The delivery system of claim 1, further comprising a sheath that is arranged to allow the medical device to pass through a lumen of the sheath when the medical device is coupled to the body member and the body locking member.

7. The delivery system of claim 1, wherein each of the enlarged portions comprises a radial protrusion.

* * * * *